US008785614B2

(12) United States Patent
Goggins et al.

(10) Patent No.: US 8,785,614 B2
(45) Date of Patent: Jul. 22, 2014

(54) ABERRANTLY METHYLATED GENES IN PANCREATIC CANCER

(75) Inventors: Michael G. Goggins, Baltimore, MD (US); Norihiro Sato, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 576 days.

(21) Appl. No.: 12/351,709

(22) Filed: Jan. 9, 2009

(65) Prior Publication Data

US 2011/0003284 A1    Jan. 6, 2011

Related U.S. Application Data

(62) Division of application No. 10/548,976, filed as application No. PCT/US2004/008061 on Mar. 17, 2004, now Pat. No. 7,485,418.

(60) Provisional application No. 60/454,614, filed on Mar. 17, 2003.

(51) Int. Cl.
*C07H 21/04* (2006.01)
*A01N 59/02* (2006.01)

(52) U.S. Cl.
USPC .......................................... 536/24.3; 424/711

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 5,786,146 A | 7/1998 | Herman et al. | |
| 6,017,704 A | 1/2000 | Herman et al. | |
| 6,200,756 B1 | 3/2001 | Herman et al. | |
| 6,265,171 B1 | 7/2001 | Herman et al. | |
| 6,953,783 B1 | 10/2005 | Besterman et al. | |
| 7,153,653 B2 | 12/2006 | Goggins et al. | |
| 2003/0104464 A1* | 6/2003 | Berlin et al. | 435/6 |
| 2003/0224040 A1* | 12/2003 | Baylin et al. | 424/450 |
| 2004/0234960 A1* | 11/2004 | Olek et al. | 435/6 |
| 2004/0234973 A1* | 11/2004 | Adorjan et al. | 435/6 |

OTHER PUBLICATIONS

Lander et al. Initial sequencing and analysis of the human genome. Nature (2001) vol. 409, pp. 860-921.*
Lander et al. Homo sapiens chromosome 9, GRCh37.p2 primer reference assembly, gene FOXE1, NCBI Reference Sequence: NC_000009.11 (2001).*
Antequera et al., "Number of CpG Islands and Genes in Human and Mouse", *Proc. Natl. Acad. Sci. USA*, 90:11995-11999 (1993).
Baylin et al., "Abnormal Patterns of DNA Methylation in Human Neoplasia: Potential Consequences for Tumor Progression", *Cancer Cells*, 3:383-390 (1991).
Baylin et al., "Alterations in DNA Methylation: A Fundamental Aspect of Neoplasia", *Adv. Cancer Res.*, 72:141-196 (1998).
Belinsky et al., "Aberrant Methylation of p16$^{INK4a}$ is an Early Event in Lung Cancer and a Potential Biomarker for Early Diagnosis", *Proc. Natl. Acad. Sci. USA*, 95:11891-11896 (1998).
Bittencourt et al., "Methylation status in the promoter region of the human PGP9.5 gene in cancer and normal tissues", *Cancer Lett.*, 170:73-79 (2001).
Cameron et al., "Synergy of Demethylation and History Deacetylase Inhibition in the Re-Expression of Genes Silenced in Cancer", *Nature Genetics*, 21:103-107 (1999).
Costello et al., "Aberrant CpG-Island Methylation Has Non-Random and Tumor-Type-Specific Paterns", *Nat. Genet.*, 25:132-138 (2000).
De Bustros et al., "The Short Arm of Chromosome 11 is a "Hot Spot" for Hypermethylation in Human Neoplasia", *Proc. Natl. Acad. Sci. USA*, 85:5693-5697 (1988).
El-Osta et al., "Precipitous Release of Methyl-CpG Binding Protein 2 and Histone Deacetylase 1 from the Methylated Human Multidrug Resistane Gene (MDR1) on Activation", *Mol. Cell Biol.*, 22:1844-1857 (2002).
Fearon and Vogelstein et al., "A Genetic Model for Colorectal Tumorigenesis", *Cell*, 61:759-767 (1990).
Fukushima et al., "Diagnosing pancreatic cancer using methylation specific PCR analysis of pancreatic juice", *Cancer Biol. Therapy*, 2:78-83 (2003).
Fukushima et al., "Aberrant Methylation of Suppresor of Cytokine Signalling-1 (SOCS-1) Gene in Pancreatic Ductal Neoplasms", *Br. J. Cancer*, 89:338-343 (2003).
Goggins et al., "Progress in Cancer Genetics: Lessons in Pancreatic Cancer", *Ann. Oncol.*, 10:4-8 (1999).
Graff et al., "E-Cadherin Expression Is Silenced by DNA Hypermethylation in Human Breast and Protate Carcinomas", *Cancer Res.*, 55:5195-5199 (1995).
Han et al., "Identification of differently expressed genes in pancreatic cancer cells using cDNA microarray", *Cancer Res.*, 62:2890-2896 (2002).
Hedrick et al., "Isolation of cDNA Clones Encoding T Cell-Specific Membrane-Associated Proteins", *Nature*, 308:149-153 (1984).
Herman et al., "Hypermethylation-Associated Inactivation Indicates a Tumor Suppressor Role for p15$^{INK4B1}$", *Cancer Res.*, 65:722-727 (1996).
Herman et al., "Inactivation of the CDKN2/p16/MTS1 Gene Is Frequently Associated with Aberrant DNA Methylation in all Human Cancers", *Cancer Res.*, 55:4525-4530 (1995).

(Continued)

*Primary Examiner* — Kenneth R. Horlick
*Assistant Examiner* — David Thomas
(74) *Attorney, Agent, or Firm* — DLA Piper LLP (US)

(57) ABSTRACT

The present invention provides a method for detecting pancreatic carcinoma in a subject. The method includes contacting a nucleic acid-containing specimen from the subject with an agent that provides a determination of the methylation state of at least one gene or associated regulatory region of the gene and identifying aberrant methylation of regions of the gene or regulatory region, wherein aberrant methylation is identified as being different when compared to the same regions of the gene or associated regulatory region in a subject not having the pancreatic carcinoma, thereby detecting pancreatic carcinoma in the subject.

9 Claims, 4 Drawing Sheets

(56) References Cited

OTHER PUBLICATIONS

Herman et al., "Methylation-Specific PCR: A Novel PCR Assay for Methylation Status of CpG Islands", *Proc. Natl. Acad. Sci. USA*, 93:9821-9826 (1996).

Herman et al., "Silencing of the VHL Tumor-Suppressor Gene by DNA Methylation in Renal Carcinoma", *Proc. Natl. Acad. Sci. USA*, 91:9700-9704 (1994).

Holliday, Robin, "The Inheritance of Epigenetic Defects", *Science*, 238:163-170 (1987).

Iacobuzio-Donahue et al., "Exploration of Global Gene Expression Patterns in Pancreatic Adenocarcinoma Using cDNA Microarrays", *Am. J. Path.*, 162:1151-1162 (2003).

Issa et al., "Methylation of the Oestrogene Receptor CpG Island Links Ageing and Neoplasia in Human Colon", *Nature Gen.*, 7:536-540 (1994).

Jansen et al., "Aberrant Mehylation of the 5' CpG Island of TSLC1 Is Common in Pancreatic Ductal Adenocarcinoma and Is First Manifest in High-Grade PanINs", *Cancer Biol. & Ther.*, 1:293-296 (2002).

Jones and Buckley, "The Role of DNA Methylation in Cancer", *Adv. Cancer Res.*, 54:1-23 (1990).

Jones, Peter A., "DNA Methylation and Cancer", *Cancer Res.*, 46:461-466 (1986).

Lisitsyn et al., "Cloning the Differences Between Two Complex Genomes", *Science*, 259:946-951 (1993).

Makos et al., "Distinct Hypermethylation Patterns Occur at Altered Chromosome Loci in Human Lung and Colon Cancer", *Proc. Natl. Acad. Sci. USA*, 89:1929-1933 (1992).

Matsubayashi et al., "DNA Methylation Alterations in the Pancreatic Juice of Patients with Suspected Pancreatic Disease", *Cancer Res.*, 66:1208-1217 (2006).

Matsubayashi et al., "Methylation of Cyclin D2 Is Observed Frequently in Pancreatic Cancer but Is also an Age-Related Phenomenon in Gastrointestinal Tissues", *Clin. Cancer Res.*, 9:1446-1452 (2003).

Merlo et al., "5' CpG Island Methylation Is Associated with Transcriptional Silencing of the Tumor Suppressor p16/CDKN2/MTS1 in Human Cancers", *Nature Med.*, 1:686-692 (1995).

Ohtani-Fujita et al., "CpG Methylation Inactivates the Promoter Activity of the Human Retinoblastoma Tumor-Suppressor Gene", *Oncogene*, 8:1063-1067 (1993).

Rozenblum et al., "Tumor-Suppressive Pathways in Pancreatic Carcinoma", *Cancer Res.*, 57:1731-1734 (1997).

Sakai et al., "Allele-Specific Hypermethylation of the Retinoblastoma Tumor-Suppressor Gene", *Am. J. Hum. Genet.*, 48:880-888 (1991).

Sato and Goggins, "The Role Epigenetic Alterations in Pancreatic Cancer", *Journal of Hepato-Biliary-Pancreatic Surgery*, 13:286-295 (2006).

Sato et al., "Aberrant Methylation of Reprimo Correlates with Genetic Instability and Predicts Poor Prognosis in Pancreatic Ductal Adenocarcinoma", *Cancer*, 107:251-257 (2006).

Sato et al., "Discovery of Novel Targets for Aberrant Methylation in Pancreatic Carcinoma Using High-Throughput Microarray", *Cancer Res.*, 63:3735-3742 (2003).

Suzuki et al., "A Genomic Screen for Genes Upregulated by Demethylation and Histone and Deacetylase Inhibition in Human Colorectal Cancer", *Nature Gen.*, 31:141-149 (2002).

Tezel et al., "PGP9.5 as a prognostic factor in pancreatic cancer", *Clin. Cancer Res.*, 6:4764-4767 (2000).

Toyota et al., "Identification of Differentially Methylated Sequences in Colorectal Cancer by Methylated CpG Island Amplification", *Cancer Res.*, 59:2307-2312 (1999).

Ueki et al., "Hypermethylation of multiple genes in pancreatic adenocarcinoma", *Cancer Res.*, 60:1835-1839 (2000).

Ueki et al., "Aberrant CpG Island Methylation in Cancer Cell Lines Arises in the Primary Cancers from with they were Derived", *Oncogene*, 21:2114-2117 (2002).

Ueki et al., "Identification and Characterization of Differentially Methylated CpG Islands in Pancreatic Carcinoma", *Cancer Res.*, 61:8540-8546 (2001).

\* cited by examiner

SEQUENCE LISTING

<160> NUMBER OF SEQ ID NOS: 74

<210> SEQ ID NO 1
<211> LENGTH: 20
<212> TYPE: DNA
<213> ORGANISM: Artificial sequence
<220> FEATURE:
<223> OTHER INFORMATION: Primer

<400> SEQUENCE: 1
tgtgtgtggg aggatgtatg          20

<210> SEQ ID NO 2
<211> LENGTH: 24
<212> TYPE: DNA
<213> ORGANISM: Artificial sequence
<220> FEATURE:
<223> OTHER INFORMATION: Primer

<400> SEQUENCE: 2
acacatctaa aatcaactaa aaac          24

-continued

```
<210> SEQ ID NO 3
<211> LENGTH: 18
<212> TYPE: DNA
<213> ORGANISM: Artificial sequence
<220> FEATURE:
<223> OTHER INFORMATION: Primer

<400> SEQUENCE: 3
gcgtgtggga ggacgtac                                                    18

<210> SEQ ID NO 4
<211> LENGTH: 23
<212> TYPE: DNA
<213> ORGANISM: Artificial sequence
<220> FEATURE:
<223> OTHER INFORMATION: Primer

<400> SEQUENCE: 4
acatctaaaa tcgactaaaa acg                                              23

<210> SEQ ID NO 5
<211> LENGTH: 22
<212> TYPE: DNA
<213> ORGANISM: Artificial sequence
<220> FEATURE:
<223> OTHER INFORMATION: Primer

<400> SEQUENCE: 5
ttgtgagtga gtgtttagtt tg                                               22

<210> SEQ ID NO 6
<211> LENGTH: 24
<212> TYPE: DNA
<213> ORGANISM: Artificial sequence
<220> FEATURE:
<223> OTHER INFORMATION: Primer

<400> SEQUENCE: 6
taattaccta aaaccaaatt catc                                             24

<210> SEQ ID NO 7
<211> LENGTH: 19
<212> TYPE: DNA
<213> ORGANISM: Artificial sequence
<220> FEATURE:
<223> OTHER INFORMATION: Primer

<400> SEQUENCE: 7
gcgagtgagc gtttagttc                                                   19

<210> SEQ ID NO 8
<211> LENGTH: 21
<212> TYPE: DNA
<213> ORGANISM: Artificial sequence
<220> FEATURE:
<223> OTHER INFORMATION: Primer

<400> SEQUENCE: 8
tacctaaaac cgaattcatc g                                                21

<210> SEQ ID NO 9
<211> LENGTH: 22
<212> TYPE: DNA
<213> ORGANISM: Artificial sequence
<220> FEATURE:
<223> OTHER INFORMATION: Primer
```

<400> SEQUENCE: 9
tgatagattt gtggggtaaa tg        22

<210> SEQ ID NO 10
<211> LENGTH: 21
<212> TYPE: DNA
<213> ORGANISM: Artificial sequence
<220> FEATURE:
<223> OTHER INFORMATION: Primer

<400> SEQUENCE: 10
cccaaaacca tactacacaa c        21

<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11
gatagattcg cggggtaaac        20

<210> SEQ ID NO 12
<211> LENGTH: 18
<212> TYPE: DNA
<213> ORGANISM: Artificial sequence
<220> FEATURE:
<223> OTHER INFORMATION: Primer

<400> SEQUENCE: 12
tacgcgacgc cctaaacg        18

<210> SEQ ID NO 13
<211> LENGTH: 22
<212> TYPE: DNA
<213> ORGANISM: Artificial sequence
<220> FEATURE:
<223> OTHER INFORMATION: Primer

<400> SEQUENCE: 13
gttaggtggg tttttttttga tg        22

<210> SEQ ID NO 14
<211> LENGTH: 20
<212> TYPE: DNA
<213> ORGANISM: Artificial sequence
<220> FEATURE:
<223> OTHER INFORMATION: Primer

<400> SEQUENCE: 14
tccataaccc tccaacaaac        20

<210> SEQ ID NO 15
<211> LENGTH: 20
<212> TYPE: DNA
<213> ORGANISM: Artificial sequence
<220> FEATURE:
<223> OTHER INFORMATION: Primer

<400> SEQUENCE: 15
ttaggcgggt tttttcgac        20

<210> SEQ ID NO 16
<211> LENGTH: 19

```
<212> TYPE: DNA
<213> ORGANISM: Artificial sequence
<220> FEATURE:
<223> OTHER INFORMATION: Primer

<400> SEQUENCE: 16
cataaccctc cgacgaacg                                                       19

<210> SEQ ID NO 17
<211> LENGTH: 22
<212> TYPE: DNA
<213> ORGANISM: Artificial sequence
<220> FEATURE:
<223> OTHER INFORMATION: Primer

<400> SEQUENCE: 17
tttgtagggt tggagattta tg                                                   22

<210> SEQ ID NO 18
<211> LENGTH: 25
<212> TYPE: DNA
<213> ORGANISM: Artificial sequence
<220> FEATURE:
<223> OTHER INFORMATION: Primer

<400> SEQUENCE: 18
aaaacaaaac aaaaacaaca aaatc                                                25

<210> SEQ ID NO 19
<211> LENGTH: 20
<212> TYPE: DNA
<213> ORGANISM: Artificial sequence
<220> FEATURE:
<223> OTHER INFORMATION: Primer

<400> SEQUENCE: 19
tcgtagggtt ggagatttac                                                      20

<210> SEQ ID NO 20
<211> LENGTH: 21
<212> TYPE: DNA
<213> ORGANISM: Artificial sequence
<220> FEATURE:
<223> OTHER INFORMATION: Primer

<400> SEQUENCE: 20
gaaacgaaaa caacgaaatc g                                                    21

<210> SEQ ID NO 21
<211> LENGTH: 24
<212> TYPE: DNA
<213> ORGANISM: Artificial sequence
<220> FEATURE:
<223> OTHER INFORMATION: Primer

<400> SEQUENCE: 21
ttattaagtg tttttgtgga tatg                                                 24

<210> SEQ ID NO 22
<211> LENGTH: 23
<212> TYPE: DNA
<213> ORGANISM: Artificial sequence
<220> FEATURE:
<223> OTHER INFORMATION: Primer

<400> SEQUENCE: 22
```

```
cctaaaaaaa caaaactcaa ctc                                         23

<210> SEQ ID NO 23
<211> LENGTH: 22
<212> TYPE: DNA
<213> ORGANISM: Artificial sequence
<220> FEATURE:
<223> OTHER INFORMATION: Primer

<400> SEQUENCE: 23
tattaagcgt tttcgtggat ac                                          22

<210> SEQ ID NO 24
<211> LENGTH: 22
<212> TYPE: DNA
<213> ORGANISM: Artificial sequence
<220> FEATURE:
<223> OTHER INFORMATION: Primer

<400> SEQUENCE: 24
cgacctaaaa aaacaaaact cg                                          22

<210> SEQ ID NO 25
<211> LENGTH: 25
<212> TYPE: DNA
<213> ORGANISM: Artificial sequence
<220> FEATURE:
<223> OTHER INFORMATION: Primer

<400> SEQUENCE: 25
gtgttttttt tgtaatttga gtttg                                       25

<210> SEQ ID NO 26
<211> LENGTH: 25
<212> TYPE: DNA
<213> ORGANISM: Artificial sequence
<220> FEATURE:
<223> OTHER INFORMATION: Primer

<400> SEQUENCE: 26
aacccacaaa aaataaaaa tcaac                                        25

<210> SEQ ID NO 27
<211> LENGTH: 22
<212> TYPE: DNA
<213> ORGANISM: Artificial sequence
<220> FEATURE:
<223> OTHER INFORMATION: Primer

<400> SEQUENCE: 27
gtttttttcg taattcgagt tc                                          22

<210> SEQ ID NO 28
<211> LENGTH: 22
<212> TYPE: DNA
<213> ORGANISM: Artificial sequence
<220> FEATURE:
<223> OTHER INFORMATION: Primer

<400> SEQUENCE: 28
cgcgaaaaaa taaaaatcaa cg                                          22

<210> SEQ ID NO 29
<211> LENGTH: 22
<212> TYPE: DNA
<213> ORGANISM: Artificial sequence
```

```
<220> FEATURE:
<223> OTHER INFORMATION: Primer

<400> SEQUENCE: 29
ggtggtggta gtttttatta tg                                      22

<210> SEQ ID NO 30
<211> LENGTH: 23
<212> TYPE: DNA
<213> ORGANISM: Artificial sequence
<220> FEATURE:
<223> OTHER INFORMATION: Primer

<400> SEQUENCE: 30
atccatatcc acaaataaaa acc                                     23

<210> SEQ ID NO 31
<211> LENGTH: 20
<212> TYPE: DNA
<213> ORGANISM: Artificial sequence
<220> FEATURE:
<223> OTHER INFORMATION: Primer

<400> SEQUENCE: 31
gcggcggtag tttttattac                                         20

<210> SEQ ID NO 32
<211> LENGTH: 21
<212> TYPE: DNA
<213> ORGANISM: Artificial sequence
<220> FEATURE:
<223> OTHER INFORMATION: Primer

<400> SEQUENCE: 32
aaaccgctaa aaaaaccaac g                                       21

<210> SEQ ID NO 33
<211> LENGTH: 21
<212> TYPE: DNA
<213> ORGANISM: Artificial sequence
<220> FEATURE:
<223> OTHER INFORMATION: Primer

<400> SEQUENCE: 33
aagaaagggt gtgtggattt g                                       21

<210> SEQ ID NO 34
<211> LENGTH: 22
<212> TYPE: DNA
<213> ORGANISM: Artificial sequence
<220> FEATURE:
<223> OTHER INFORMATION: Primer

<400> SEQUENCE: 34
ccacactatc atctcaaaaa tc                                      22

<210> SEQ ID NO 35
<211> LENGTH: 18
<212> TYPE: DNA
<213> ORGANISM: Artificial sequence
<220> FEATURE:
<223> OTHER INFORMATION: Primer

<400> SEQUENCE: 35
gaaagggcgc gcggattc                                           18
```

<210> SEQ ID NO 36
<211> LENGTH: 20
<212> TYPE: DNA
<213> ORGANISM: Artificial sequence
<220> FEATURE:
<223> OTHER INFORMATION: Primer

<400> SEQUENCE: 36
cgctatcgtc tcgaaaatcg                                         20

<210> SEQ ID NO 37
<211> LENGTH: 21
<212> TYPE: DNA
<213> ORGANISM: Artificial sequence
<220> FEATURE:
<223> OTHER INFORMATION: Primer

<400> SEQUENCE: 37
gtttgggttt gggagatatt g                                       21

<210> SEQ ID NO 38
<211> LENGTH: 22
<212> TYPE: DNA
<213> ORGANISM: Artificial sequence
<220> FEATURE:
<223> OTHER INFORMATION: Primer

<400> SEQUENCE: 38 ccccttctt aaaacaatca ac                                       22

<210> SEQ ID NO 39
<211> LENGTH: 20
<212> TYPE: DNA
<213> ORGANISM: Artificial sequence
<220> FEATURE:
<223> OTHER INFORMATION: Primer

<400> SEQUENCE: 39
gtttgggttc gggagatatc                                         20

<210> SEQ ID NO 40
<211> LENGTH: 21
<212> TYPE: DNA
<213> ORGANISM: Artificial sequence
<220> FEATURE:
<223> OTHER INFORMATION: Primer

<400> SEQUENCE: 40
cctttcttaa aacgatcaac g                                       21

<210> SEQ ID NO 41
<211> LENGTH: 21
<212> TYPE: DNA
<213> ORGANISM: Artificial sequence
<220> FEATURE:
<223> OTHER INFORMATION: Primer

<400> SEQUENCE: 41
gggtgtattt agtttgtagt g                                       21

<210> SEQ ID NO 42
<211> LENGTH: 20
<212> TYPE: DNA
<213> ORGANISM: Artificial sequence
<220> FEATURE:
<223> OTHER INFORMATION: Primer

```
<400> SEQUENCE: 42 caatccccccc aaccaataac                                              20

<210> SEQ ID NO 43
<211> LENGTH: 19
<212> TYPE: DNA
<213> ORGANISM: Artificial sequence
<220> FEATURE:
<223> OTHER INFORMATION: Primer

<400> SEQUENCE: 43
gtcggggcgt atttagttc                                                19

<210> SEQ ID NO 44
<211> LENGTH: 18
<212> TYPE: DNA
<213> ORGANISM: Artificial sequence
<220> FEATURE:
<223> OTHER INFORMATION: Primer

<400> SEQUENCE: 44 tcccccccgac caataacg                                                18

<210> SEQ ID NO 45
<211> LENGTH: 20
<212> TYPE: DNA
<213> ORGANISM: Artificial sequence
<220> FEATURE:
<223> OTHER INFORMATION: Primer

<400> SEQUENCE: 45
gtgttagggt gagggtattg                                               20

<210> SEQ ID NO 46
<211> LENGTH: 22
<212> TYPE: DNA
<213> ORGANISM: Artificial sequence
<220> FEATURE:
<223> OTHER INFORMATION: Primer

<400> SEQUENCE: 46
actcacaaat ctcacaaaca tc                                            22

<210> SEQ ID NO 47
<211> LENGTH: 18
<212> TYPE: DNA
<213> ORGANISM: Artificial sequence
<220> FEATURE:
<223> OTHER INFORMATION: Primer

<400> SEQUENCE: 47
cgttagggcg agggtatc                                                 18

<210> SEQ ID NO 48
<211> LENGTH: 19
<212> TYPE: DNA
<213> ORGANISM: Artificial sequence
<220> FEATURE:
<223> OTHER INFORMATION: Primer

<400> SEQUENCE: 48
ctcgcgaatc tcacaaacg                                                19

<210> SEQ ID NO 49
```

```
<211> LENGTH: 23
<212> TYPE: DNA
<213> ORGANISM: Artificial sequence
<220> FEATURE:
<223> OTHER INFORMATION: Primer

<400> SEQUENCE: 49
tgtggatgtg attgttatta ttg                                           23

<210> SEQ ID NO 50
<211> LENGTH: 22
<212> TYPE: DNA
<213> ORGANISM: Artificial sequence
<220> FEATURE:
<223> OTHER INFORMATION: Primer

<400> SEQUENCE: 50
tctccataac cacaataact tc                                            22

<210> SEQ ID NO 51
<211> LENGTH: 20
<212> TYPE: DNA
<213> ORGANISM: Artificial sequence
<220> FEATURE:
<223> OTHER INFORMATION: Primer

<400> SEQUENCE: 51
cggatgcgat cgttattatc                                               20

<210> SEQ ID NO 52
<211> LENGTH: 19
<212> TYPE: DNA
<213> ORGANISM: Artificial sequence
<220> FEATURE:
<223> OTHER INFORMATION: Primer

<400> SEQUENCE: 52
cgtaaccgcg ataacttcg                                                19

<210> SEQ ID NO 53
<211> LENGTH: 22
<212> TYPE: DNA
<213> ORGANISM: Artificial sequence
<220> FEATURE:
<223> OTHER INFORMATION: Primer

<400> SEQUENCE: 53
ttgtgggtta gagtattgtt tg                                            22

<210> SEQ ID NO 54
<211> LENGTH: 21
<212> TYPE: DNA
<213> ORGANISM: Artificial sequence
<220> FEATURE:
<223> OTHER INFORMATION: Primer

<400> SEQUENCE: 54
atctcctcac accaacattt c                                             21

<210> SEQ ID NO 55
<211> LENGTH: 20
<212> TYPE: DNA
<213> ORGANISM: Artificial sequence
```

```
<220> FEATURE:
<223> OTHER INFORMATION: Primer

<400> SEQUENCE: 55
tgcgggttag agtattgttc                                                    20

<210> SEQ ID NO 56
<211> LENGTH: 18
<212> TYPE: DNA
<213> ORGANISM: Artificial sequence
<220> FEATURE:
<223> OTHER INFORMATION: Primer

<400> SEQUENCE: 56
cctcgcaccg acatttcg                                                      18

<210> SEQ ID NO 57
<211> LENGTH: 24
<212> TYPE: DNA
<213> ORGANISM: Artificial sequence
<220> FEATURE:
<223> OTHER INFORMATION: Primer

<400> SEQUENCE: 57
tttgtattta tttggttgtg attg                                               24

<210> SEQ ID NO 58
<211> LENGTH: 24
<212> TYPE: DNA
<213> ORGANISM: Artificial sequence
<220> FEATURE:
<223> OTHER INFORMATION: Primer

<400> SEQUENCE: 58
cccaaactac aactataaaa cacc                                               24

<210> SEQ ID NO 59
<211> LENGTH: 20
<212> TYPE: DNA
<213> ORGANISM: Artificial sequence
<220> FEATURE:
<223> OTHER INFORMATION: Primer

<400> SEQUENCE: 59
ttatttggtc gcgatcgttc                                                    20

<210> SEQ ID NO 60
<211> LENGTH: 22
<212> TYPE: DNA
<213> ORGANISM: Artificial sequence
<220> FEATURE:
<223> OTHER INFORMATION: Primer

<400> SEQUENCE: 60
cccaaactac aactataaaa cg                                                 22

<210> SEQ ID NO 61
<211> LENGTH: 23
<212> TYPE: DNA
<213> ORGANISM: Artificial sequence
<220> FEATURE:
<223> OTHER INFORMATION: Primer

<400> SEQUENCE: 61
tagtttggtg ttgttttatg ttg                                                23
```

```
<210> SEQ ID NO 62
<211> LENGTH: 22
<212> TYPE: DNA
<213> ORGANISM: Artificial sequence
<220> FEATURE:
<223> OTHER INFORMATION: Primer

<400> SEQUENCE: 62
ccccaaaacc atctatcaat ac                                              22

<210> SEQ ID NO 63
<211> LENGTH: 20
<212> TYPE: DNA
<213> ORGANISM: Artificial sequence
<220> FEATURE:
<223> OTHER INFORMATION: Primer

<400> SEQUENCE: 63
gtagttcggc gtcgttttac                                                 20

<210> SEQ ID NO 64
<211> LENGTH: 20
<212> TYPE: DNA
<213> ORGANISM: Artificial sequence
<220> FEATURE:
<223> OTHER INFORMATION: Primer

<400> SEQUENCE: 64
cgaaaccgtc tatcgatacg                                                 20

<210> SEQ ID NO 65
<211> LENGTH: 21
<212> TYPE: DNA
<213> ORGANISM: Artificial sequence
<220> FEATURE:
<223> OTHER INFORMATION: Primer

<400> SEQUENCE: 65
ctctgtttag cactgataat g                                               21

<210> SEQ ID NO 66
<211> LENGTH: 22
<212> TYPE: DNA
<213> ORGANISM: Artificial sequence
<220> FEATURE:
<223> OTHER INFORMATION: Primer

<400> SEQUENCE: 66
tttattagac ttgagctgat tc                                              22

<210> SEQ ID NO 67
<211> LENGTH: 19
<212> TYPE: DNA
<213> ORGANISM: Artificial sequence
<220> FEATURE:
<223> OTHER INFORMATION: Primer

<400> SEQUENCE: 67
catcgagctg ctcatcaac                                                  19

<210> SEQ ID NO 68
<211> LENGTH: 19
<212> TYPE: DNA
<213> ORGANISM: Artificial sequence
```

```
<220> FEATURE:
<223> OTHER INFORMATION: Primer

<400> SEQUENCE: 68
ctgctcttgt ccaaggatc                                                    19

<210> SEQ ID NO 69
<211> LENGTH: 19
<212> TYPE: DNA
<213> ORGANISM: Artificial sequence
<220> FEATURE:
<223> OTHER INFORMATION: Primer

<400> SEQUENCE: 69
ctggcccgag atgcttaag                                                    19

<210> SEQ ID NO 70
<211> LENGTH: 22
<212> TYPE: DNA
<213> ORGANISM: Artificial sequence
<220> FEATURE:
<223> OTHER INFORMATION: Primer

<400> SEQUENCE: 70
tattttcatc ctcagtgcaa ac                                                22

<210> SEQ ID NO 71
<211> LENGTH: 20
<212> TYPE: DNA
<213> ORGANISM: Artificial sequence
<220> FEATURE:
<223> OTHER INFORMATION: Primer

<400> SEQUENCE: 71
cttcatgaag cagaccattg                                                   20

<210> SEQ ID NO 72
<211> LENGTH: 19
<212> TYPE: DNA
<213> ORGANISM: Artificial sequence
<220> FEATURE:
<223> OTHER INFORMATION: Primer

<400> SEQUENCE: 72
atcatgggct gcctgtatg                                                    19

<210> SEQ ID NO 73
<211> LENGTH: 19
<212> TYPE: DNA
<213> ORGANISM: Artificial sequence
<220> FEATURE:
<223> OTHER INFORMATION: Primer

<400> SEQUENCE: 73
cgggagatca agcagaatc                                                    19

<210> SEQ ID NO 74
<211> LENGTH: 19
<212> TYPE: DNA
<213> ORGANISM: Artificial sequence
<220> FEATURE:
<223> OTHER INFORMATION: Primer

<400> SEQUENCE: 74
aacggcctcg ttgtacttg                                                    19
```

ABERRANTLY METHYLATED GENES IN PANCREATIC CANCER

CROSS REFERENCE TO RELATED APPLICATIONS

This application is a divisional application of U.S. application Ser. No. 10/548,976 filed Jun. 23, 2006, now U.S. Pat. No. 7,485,418; which is a 35 USC §371 National Stage application of International Application No. PCT/US2004/008061 filed Mar. 17, 2004; which claims the benefit under 35 USC §119(e) to U.S. Application Ser. No. 60/454,614 filed Mar. 17, 2003, now abandoned. The disclosure of each of the prior applications is considered part of and is incorporated by reference in the disclosure of this application.

BACKGROUND OF THE INVENTION

Field of the Invention

The present invention relates generally to the regulation of gene expression and more specifically to a method of determining the DNA methylation status of CpG sites in a given locus and correlating the methylation status with the presence of a cell proliferative disorder.

Background Information

DNA methylases transfer methyl groups from the universal methyl donor S-adenosyl methionine to specific sites on the DNA. Several biological functions have been attributed to the methylated bases in DNA. The most established biological function for methylated DNA is the protection of DNA from digestion by cognate restriction enzymes. The restriction modification phenomenon has, so far, been observed only in bacteria. Mammalian cells, however, possess a different methylase that exclusively methylates cytosine residues that are 5' neighbors of guanine (CpG). This modification of cytosine residues has important regulatory effects on gene expression, especially when involving CpG rich areas, known as CpG islands, located in the promoter regions of many genes.

Methylation has been shown by several lines of evidence to play a role in gene activity, cell differentiation, tumorigenesis, X-chromosome inactivation, genomic imprinting and other major biological processes (Razin, A., H., and Riggs, R. D. eds. in *DNA Methylation Biochemistry and Biological Significance*, Springer-Verlag, New York, 1984). In eukaryotic cells, methylation of cytosine residues that are immediately 5' to a guanosine, occurs predominantly in CG poor regions (Bird, A., Nature, 321:209, 1986). In contrast, CpG islands remain unmethylated in normal cells, except during X-chromosome inactivation (Migeon, et al., supra) and parental specific imprinting (Li, et al., Nature, 366:36, 1993) where methylation of 5' regulatory regions can lead to transcriptional repression. De novo methylation of the Rb gene has been demonstrated in a small fraction of retinoblastomas (Sakai, et al., Am. J. Hum. Genet, 48:880, 1991), and recently, a more detailed analysis of the VHL gene showed aberrant methylation in a subset of sporadic renal cell carcinomas (Herman, et al., Proc. Natl. Acad. Sci., U.S.A., 91:9700, 1994). Expression of a tumor suppressor gene can also be abolished by de novo DNA methylation of a normally unmethylated CpG island (Issa, et al., Nature Genet., 7:536, 1994; Herman, et al., supra; Merlo, et al., Nature Med., 1:686, 1995; Herman, et al., Cancer Res., 56:722, 1996; Graff, et al., Cancer Res., 55:5195, 1995; Herman, et al., Cancer Res., 55:4525, 1995).

Human cancer cells typically contain somatically altered nucleic acid, characterized by mutation, amplification, or deletion of critical genes. In addition, the nucleic acid from human cancer cells often displays somatic changes in DNA methylation (E. R. Fearon, et al., Cell, 61:759, 1990; P. A. Jones, et al., Cancer Res., 46:461, 1986; R. Holliday, Science, 238:163, 1987; A. De Bustros, et al., Proc. Natl. Acad. Sci., USA, 85:5693, 1988); P. A. Jones, et al., Adv. Cancer Res., 54:1, 1990; S. B. Baylin, et al., Cancer Cells, 3:383, 1991; M. Makos, et al., Proc. Natl. Acad. Sci., USA, 89:1929, 1992; N. Ohtani-Fujita, et al., Oncogene, 8:1063, 1993). However, the precise role of abnormal DNA methylation in human tumorigenesis has not been established. Aberrant methylation of normally unmethylated CpG islands has been described as a frequent event in immortalized and transformed cells, and has been associated with transcriptional inactivation of defined tumor suppressor genes in human cancers. In the development of colorectal cancers (CRC), a series of tumor suppressor genes (TSG) such as APC, p53, DCC and DPC4 are inactivated by mutations and chromosomal deletions. Some of these alterations result from a chromosomal instability phenotype described in a subset of CRC. Recently, an additional pathway has been shown to be involved in a familial form of CRC, hereditary non-polyposis colorectal cancer. The cancers from these patients show a characteristic mutator phenotype which causes microsatellite instability (MI), and mutations at other gene loci such as TGF-β-RII (Markowitz et al., Science, 268(5215):1336-8, 1995) and BAX. This phenotype usually results from mutations in the mismatch repair (MMR) genes hMSH2 and hMLH1. A subset of sporadic CRC also show MI, but mutations in MMR genes appear to be less frequent in these tumors.

Another molecular defect described in CRC is CpG island (CGI) methylation. CGIs are short sequences rich in the CpG dinucleotide and can be found in the 5' region of about half of all human genes. Methylation of cytosine within 5' CGIs is associated with loss of gene expression and has been seen in physiological conditions such as X chromosome inactivation and genomic imprinting. Aberrant methylation of CGIs has been detected in genetic diseases such as the fragile-X syndrome, in aging cells and in neoplasia. About half of the tumor suppressor genes which have been shown to be mutated in the germline of patients with familial cancer syndromes have also been shown to be aberrantly methylated in some proportion of sporadic cancers, including Rb, VHL, p16, hMLH1, and BRCA1, TSG methylation in cancer is usually associated with (Antequera, et al., Proc. Natl. Acad. Sci. USA, 90:11995-11999, 1993) lack of gene transcription and (Baylin, et al., Adv. Cancer Res., 72:141-196, 1998) absence of coding region mutation. Thus it has been proposed mat CGI methylation serves as an alternative mechanism of gene inactivation in cancer.

The causes and global patterns of CGI methylation in human cancers remain poorly defined. Aging could play a factor in this process because methylation of several CGIs could be detected in an age-related manner in normal colon mucosa as well as in CRC. In addition, aberrant methylation of CGIs has been associated with the MI phenotype in CRC as well as specific carcinogen exposures. However, an understanding of aberrant methylation in CRC has been somewhat limited by the small number of CGIs analyzed to date. In fact, previous studies have suggested that large numbers of CGIs are methylated in immortalized cell lines, and it is not well understood whether this global aberrant methylation is caused by the cell culture conditions or whether they are an integral part of the pathogenesis of cancer.

Most of the methods developed to date for detection of methylated cytosine depend upon cleavage of the phosphodiester bond alongside cytosine residues, using either methylation-sensitive restriction enzymes or reactive chemicals such as hydrazine which differentiate between cytosine and its 5-methyl derivative. Genomic sequencing protocols which identify a 5-MeC residue in genomic DNA as a site that is not cleaved by any of the Maxam Gilbert sequencing reactions have also been used, but still suffer disadvantages such as the requirement for large amount of genomic DNA and the difficulty in detecting a gap in a sequencing ladder which may contain bands of varying intensity.

Mapping of methylated regions in DNA has relied primarily on Southern hybridization approaches, based on the inability of methylation-sensitive restriction enzymes to cleave sequences which contain one or more methylated CpG sites. This method provides an assessment of the overall methylation status of CpG islands, including some quantitative analysis, but is relatively insensitive and requires large amounts of high molecular weight DNA.

Another method utilizes bisulfite treatment of DNA to convert all unmethylated cytosines to uracil. The altered DNA is amplified and sequenced to show the methylation status of all CpG sites. However, this method is technically difficult, labor intensive and without cloning amplified products, it is less sensitive than Southern analysis, requiring approximately 10% of the alleles to be methylated for detection.

Identification of the earliest genetic changes in tumorigenesis is a major focus in molecular cancer research. Diagnostic approaches based on identification of these changes are likely to allow implementation of early detection strategies and novel therapeutic approaches targeting these early changes might lead to more effective cancer treatment.

About half of all human genes have 5' CpG islands and these islands are usually associated with the 5' regulatory regions of genes (Antequera, et al., Proc. Natl. Acad. Sci. USA 90:11995-11999, 1993). The 5' CpG islands of most nonimprinted genes are thought to remain unmethylated in normal cells but may become methylated during aging or tumorigenesis. Through interactions between methyl CpG binding proteins, histories and histone deacetylase, 5' CpG island methylation can contribute to changes in chromatin that cause transcriptional silencing (Baylin, et al., Adv. Cancer Res. 72:141-196, 1998). Promoter methylation is implicated in the transcriptional silencing of tumor suppressor and mismatch repair genes (e.g. p16, Rb, VHL, hMLH1) in many cancers. Although 13 hypermethylated genes and clones in pancreatic cancers were previously identified (Ueki, et al., Cancer Res. 60:1835-1839, 2000), there almost certainly are others. Costello et al. have estimated that ~400 genes are aberrantly methylated in cancers and have found evidence for tumor-specific pattern of methylation (Costello, et al., Nat Genet. 24:132-138, 2000). A better description of the pattern of DNA methylation abnormalities in cancer may improve an understanding of the role of DNA methylation in tumorigenesis and identification of differentially methylated CpG islands in cancer may lead to the discovery of novel genes with tumor suppressor properties. Finally, identified genes or loci could be utilized as cancer-specific markers for the early detection of cancer (Belinsky, et al., Proc. Natl. Acad. Sci. USA 95:11891-11896, 1998).

Pancreatic cancer is the fourth leading cause of cancer death in men and in women and each year ~28,000 Americans die of the disease (Greenlee, et al., CA Cancer J. Clin. 50:7-33, 2000). Frequent genetic changes such as mutational activation of the K-ras oncogene and inactivation of the p16, DPC4, p53, MKK4, STK11, TGFBR2, and TGFBR1 tumor suppressor genes have been described in pancreatic cancer (Goggins, et al., Ann. Oncol. 10:4-8, 1999, Rozenblum, et al., Cancer Res. 52:1731-1734, 1997). Although multiple tumor suppressor pathways have been shown to play a role in pancreatic carcinogenesis, little is known about the contribution of DNA methylation to inactivation of genes in these pathways. Recently, a novel technique, methylated CpG island amplification (MCA), was developed to enrich for methylated CpG rich sequences. MCA coupled with RDA (MCA/RDA) can recover CpG islands differentially methylated in cancer cells (Toyota, et al., Cancer Res. 59:2307-2312, 1997).

SUMMARY OF THE INVENTION

The present invention is based on the finding that several genes are newly identified as being differentially methylated in pancreatic cancer. This seminal discovery is useful for cancer screening, risk-assessment, prognosis, minimal-residual disease identification, staging and identification of therapeutic targets. The identification of genes that are methylated in cancer, aging or diseases associated with aging increases the likelihood of finding genes methylated in a particular cancer; increases the sensitivity and specificity of methylation detection; allows methylation profiling using multiple genes; and allows identification of new targets for therapeutic intervention.

In one aspect of the invention, there is provided a method for detecting pancreatic carcinoma in a subject comprising contacting a nucleic acid-containing specimen from the subject with an agent that provides a determination of the methylation state of at least one gene or associated regulatory region of the gene selected from Tables 1-3 and combinations thereof; and identifying aberrant methylation of regions of the gene or regulatory region, wherein aberrant methylation is identified as being different when compared to the same regions of the gene or associated regulatory region in a subject not having the pancreatic carcinoma, thereby detecting pancreatic carcinoma in the subject. The regions of the gene or regulatory region are contained within CpG rich regions. Illustrative genes are listed in Tables 1-3. In this aspect, the aberrant methylation is hypermethylation when compared to the same regions of the gene or associated regulatory regions in a subject not having pancreatic carcinoma.

In another aspect of the invention, a pair of primers that hybridize with a target sequence in the gene or associated regulatory region of the gene are utilized to identify genes or regulatory regions associated with pancreatic cancer. In yet another aspect, the nucleic acid-containing specimen includes tissue such as pancreatic ductal epithelium, pancreatic tissue, stool, blood, or pancreatic fluid. Pancreatic carcinoma includes, but is not limited to, pancreatic ductal adenocarcinoma, chronic pancreatitis, islet cell tumor, or serus cystadenoma.

In another aspect of the invention, a method of identifying at least one gene silenced by DNA methylation associated with pancreatic carcinoma includes contacting an array of nucleotide sequences representative of a genome with nucleic acid molecules corresponding to RNA expressed in cancer cells contacted with at least one agent that reactivates expression of silenced genes but not RNA expressed in normal cells corresponding to the cancer cells, under conditions suitable for selective hybridization of nucleic acid subtraction products to complementary nucleotide sequences of the array; and detecting selective hybridization of nucleic acid to a subpopulation of nucleotide sequences of the array, wherein nucleic acid molecules corresponding to RNA expressed in the normal cells corresponding the cancer cells do not hybridize to the subpopulation of nucleotide sequences under the conditions suitable for selective hybridization, whereby the nucleic acid molecules that selectively hybridize to the subpopulation of nucleotide sequences of the array represent epigenetically silenced genes of the cancer cells, thereby identifying at least one epigenetically silenced gene associated with pancreatic cancer.

Determining the methylation state of the gene includes contacting the nucleic acid-containing specimen with an agent that modifies methylated cytosine, amplifying a CpG-containing nucleic acid in the specimen by means of CpG-specific oligonucleotide primers, wherein the oligonucleotide primers distinguish between modified methylated and nonmethylated nucleic acid, and detecting the methylated nucleic acid based on the presence or absence of amplification products produced in the amplifying step. The method includes optionally contacting the amplification products with a methylation sensitive restriction endonuclease. Other methods for determining methylation status of a gene and/or regulatory sequences are well known in the art and are described more fully herein.

In one aspect, the methylating agent 5 aza 2' deoxycytidine (5Aza-dC) is used to treat cells for further determination of the methylation status. In another aspect, the histone deacetylase inhibitor trichostatin (TSA) is used to treat cells for further determination of the methylation status. In yet another aspect, a combination of 5 aza 2' deoxycytidine (5Aza-dC) and trichostatin (TSA) is utilized. Genes associated with pancreatic carcinoma are listed in Tables 1-3 by way of example. Specifically, such genes include CDH3, reprimo, CLDN5, DR3, FOXE1, LDOC1, LHX1, NEFH, NPTX2, PIG11, SARP2, ST14, SMARCA1, TJP2, UCHL1, WNT7A, or a combination thereof.

In another aspect of the invention, an amplification primer pair is provided The amplification primer pair includes a forward primer and a reverse primer as set forth in SEQ ID NOS: 1 to 64, wherein the amplification primer pair amplifies a portion of a gene of Tables 1-3. In one aspect, the amplification primer pair specifically amplifies a methylated 5' regulatory region of the nucleic acid molecule. More specifically, these amplification primer pairs include SEQ ID NOS: 3 and 4, SEQ ID NOS: 7 and 8, SEQ ID NOS: 11 and 12, SEQ ID NOS: 15 and 16, SEQ ID NOS: 19 and 20, SEQ ID NOS: 23 and 24, SEQ ID NOS: 27 and 28, SEQ ID NOS: 31 and 32, SEQ ID NOS: 35 and 36, SEQ ID NOS: 39 and 40, SEQ ID NOS: 43 and 44, SEQ ID NOS: 47 and 48, SEQ ID NOS: 51 and 52, SEQ ID NOS: 55 and 56, SEQ ID NOS: 59 and 60 or SEQ ID NOS: 63 and 64. In another aspect of the invention, the amplification primer pair specifically amplifies a unmethylated 5' regulatory region of the nucleic acid molecule. More specifically, these amplification primer pairs include SEQ ID NOS: 1 and 2, SEQ ID NOS: 5 and 6, SEQ ID NOS: 9 and 10, SEQ ID NOS: 13 and 14, SEQ ID NOS: 17 and 18, SEQ ID NOS: 21 and 22, SEQ ID NOS: 25 and 26, SEQ ID NOS: 29 and 30, SEQ ID NOS: 33 and 34, SEQ ID NOS: 37 and 38, SEQ ID NOS: 41 and 42, SEQ ID NOS: 45 and 46, SEQ ID NOS: 49 and 50, SEQ ID NOS: 53 and 54, SEQ ID NOS: 57 and 58, or SEQ ID NOS: 61 and 62.

Also included are target sequences to which the amplification primers bind.

In another aspect, a method for monitoring a therapeutic regimen for treating a subject having pancreatic cancer is provided. The method includes a) obtaining a nucleic acid-containing specimen from the subject prior to therapy; b) contacting the nucleic acid-containing specimen with an agent that provides a determination of the methylation state of at least one gene or associated regulatory region of the gene; c) identifying aberrant methylation of regions of the gene or regulatory region, wherein aberrant methylation is identified as being different when compared to the same regions of the gene or associated regulatory region in a subject not having the pancreatic cancer; and d) determining a change in the methylation state of the gene during therapy, wherein the change is determined by comparing the methylation state of the gene with the methylation state of the same gene from the nucleic acid-containing sample from the same subject prior to therapy, thereby monitoring a therapeutic regimen for treating a pancreatic cancer subject.

Another aspect of the invention provides a kit containing at least one amplification primer pair including a methylation specific amplification primer pair, an unmethylated specific amplification primer pair, or a combination comprising at least one methylation specific amplification primer pair and at least one unmethylation specific amplification primer pair. The kit further includes a reagent that modifies methylated cytosine residues. In another aspect of the invention, the kit further comprises a methylation sensitive restriction endonuclease. In yet another embodiment, the kit comprises reagents for performing an amplification reaction. Optionally, the kit includes 5-aza-2'-deoxycytidine and/or trichostatin A.

Another aspect of the invention provides a kit useful for the detection of pancreatic carcinoma in a subject including a carrier means compartmentalized to receive a sample therein; one or more containers comprising a first container containing a reagent which modifies unmethylated cytosine and a second container containing primers for amplification of a CpG-containing nucleic acid, wherein the primers are pairs from SEQ ID NO:1-64. In one aspect of the invention, the kit includes a third container containing a methylation sensitive restriction endonuclease. In this aspect, the modifying reagent is typically bisulfate. In another illustrative example, the primer hybridizes with a target sequence as set forth in Tables 1-3.

Another aspect of the invention provides a gene associated with pancreatic carcinoma as listed in Tables 1-3, wherein associated regulatory sequences contain CpG-rich regions. In one aspect, the state of methylation of the CpG-rich regions is determinative of the presence of pancreatic carcinoma in a subject from which the nucleic acid molecule is isolated. In one aspect, hypermethylation of the CpG-rich regions is indicative of the presence of pancreatic carcinoma in a subject from which the nucleic acid is isolated.

BRIEF DESCRIPTION OF THE INVENTION

FIG. 1A shows RT-PCR analysis of five genes (CDH3, NPTX2, SARP2, UCHL1 and WNT7A) in pancreatic cancer cell lines (AsPC1, and MiaPaCa2). Cells were treated with 5Aza-dC alone, TSA alone, or a combination of both and subjected to RNA extraction. Glyceraldehyde-3-phospate dehydrogenase (GAPDH) serves as a RNA control.

DETAILED DESCRIPTION OF THE INVENTION

Figure 1A:
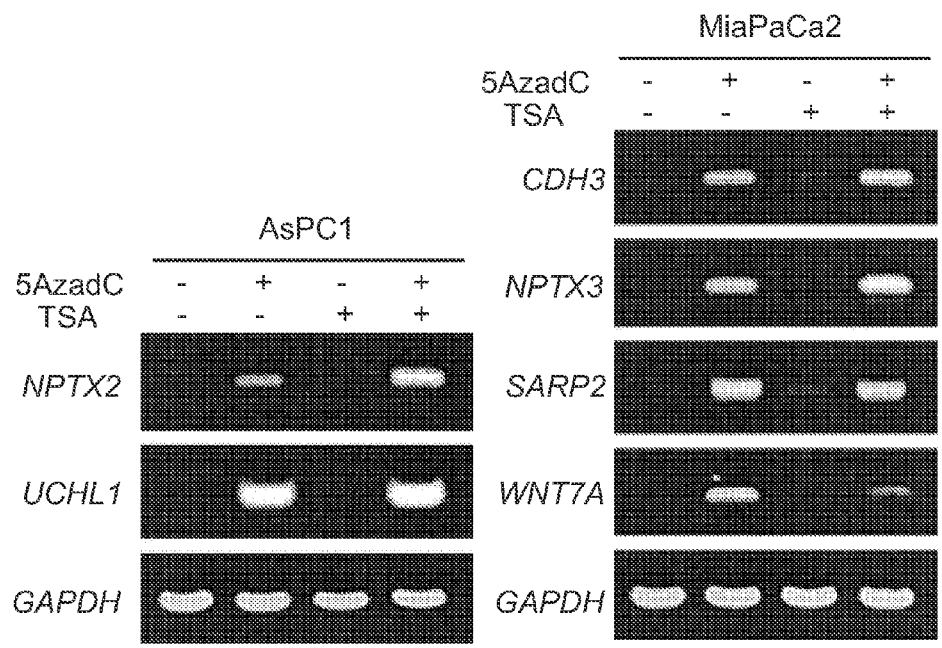
FIG. 1B shows MSP analysis of five genes (CDH3, CLDN5, NPTX2, SARP2, and TJP2) in pancreatic cancer cell lines and a nonneoplastic ductal cell line (HPDE). The PGR products in Lances U and M indicated the presence of unmethylated and methylated templates, respectively.

It has been determined that an aberrant methylation state and/or histone deacetylase (HDAC) activity (with the methylation being predominant) of nucleic acids in certain genes, particularly regulatory sequences, is diagnostic for the presence or potential development of a cellular proliferative disorder in subjects bearing the aberrantly methylated nucleic acids. More particularly, the hypermethylation of certain nucleotides localized in CpG islands has been shown to affect the expression of genes associated with the CpG islands; typically such hypermethylated genes have reduced or abolished expression, primarily due to down-regulated transcription. Using a well known technique called methylation specific PCR (MSP), several nucleic acid molecules aberrantly methylated in pancreatic cancer cells were identified.

The presently disclosed microarray based strategy obviates the disadvantages of previous methods by coupling gene expression status to epigenetic regulation. Furthermore, the approach exploits the observation that global changes in gene expression in cancer genes can be dependent on both dense CpG island methylation and HDAC activity (Cameron et al., Nature Genet 21:103-107, 1999, which is incorporated herein by reference). The disclosed methods robustly identify genes for which transcriptional repression can have a key role in tumorigenesis. Remarkably, the disclosed genomic screening method allowed an identification of gene hypermethylation events that cluster to specific tumor types, and can simultaneously involve multiple members of a single gene family.

As used herein, a global change in gene expression refers to a change in any function normally attributed to a cell containing the gene Such global changes in gene expression include, but are not limited to, reactivation of a gene that is epigenetically silenced. The term "epigenetically silenced" or "epigenetic silenced", when used in reference to a gene, means that the gene is not being transcribed, or is being transcribed at a level that is decreased with respect to the level of transcription of the gene in a corresponding control cell (e.g., a normal cell), due to a mechanism other than a genetic change. Epigenetic mechanisms of gene silencing are well known and include, for example, hypermethylation of CpG dinucleotides in a CpG island of the 5' regulatory region of a gene, and structural changes in chromatin due, for example, to histone acetylation, such that gene transcription is reduced or inhibited. Methods for detecting epigenetic silencing of a gene are disclosed herein and include, for example, detecting re-expression (reactivation) of the gene following contact of a cell with an agent that relieves the epigenetic silencing, for example, with a demethylating agent where the silencing is due to hypermethylation.

Methylated nucleic acid sequences are also provided. As used herein, the term "methylation" or "hypermethylation", when used in reference to a gene, means that cytosine residues of CpG dinucleotides in a CpG island associated with the gene are methylated at the 5'-position, i.e., 5'-methylcytosine. The term "methylation status" is used herein to refer to a relative abundance, including the presence or absence, of methylated cytosine residues of CpG dinucleotides in a CpG island. In general, the cytosine residues in a CpG island are not methylated in a transcriptionally active gene and, therefore, the detection of methylated cytosine residues in a CpG island indicates that expression of the gene is reduced or inhibited. Accordingly, as discussed above, reference herein to a "methylation silenced" gene means that the gene is not being transcribed, or is being transcribed at a level that is decreased with respect to the level of transcription of the gene in a corresponding control cell (generally a normal cell) due to hypermethylation of CpG dinucleotides in a CpG island of the 5' regulatory region of the gene. A consequence of methylation silenced gene expression is that a cell containing the gene has reduced levels of, or completely lacks, a polypeptide encoded by the gene (i.e., the gene product) such that any function normally attributed to the gene product in the cell is reduced or absent.

In one embodiment of the invention, a method of identifying an epigenetically silenced gene associated with a cancer can be performed, for example, by contacting an array of nucleotide sequences representative of a genome with nucleic acid subtraction products (i.e., nucleic acid molecules corresponding to RNA expressed in cancer cells contacted with at least one agent that reactivates expression of epigenetically silenced genes, but not RNA expressed in normal cells corresponding to the cancer cells) under conditions suitable for selective hybridization of nucleic acid subtraction products to complementary nucleotide sequences of the array; and detecting selective hybridization of nucleic acid subtraction products to a subpopulation of nucleotide sequences of the array, wherein nucleic acid molecules corresponding to RNA expressed in the normal cells corresponding to the cancer cells do not hybridize to the subpopulation of nucleotide sequences under such conditions suitable for selective hybridization, whereby the nucleic acid subtraction products that selectively hybridize to the subpopulation of nucleotide sequences of the array represent epigenetically silenced genes of the cancer cells.

Reference to "nucleic acid molecules corresponding to RNA" of a cell means RNA such as mRNA or polyA+ RNA, cDNA generated using RNA from the cell as a template, or cRNA generated using RNA or cDNA as a template. For practicing a method of the invention, the nucleic acid molecules corresponding to RNA of a cell generally are detectably labeled, for example, with a radioisotope, a paramagnetic isotope, a luminescent compound, a chemiluminescent compound, a fluorescent compound, a metal chelate, an enzyme, a substrate for an enzyme, a receptor, or a ligand for a receptor, or are capable of being detected, for example, using a detectably labeled probe, such that hybridization of the nucleic acid molecules to nucleotide sequences of the array can be detected.

As used herein, the term "array of nucleotide sequences representative of a genome" means an organized group of nucleotide sequences that are linked to a solid support, for example, a microchip or a glass slide, wherein the sequences can hybridize specifically and selectively to nucleic acid molecules expressed in a cell. The array is selected based on the organism from which the cells to be examined are derived and/or on a tissue or tissues that are to be examined. Generally, the array is representative of the genome of a eukaryotic cell or cell type, particularly a mammalian cell or cell type, and preferably a human cell, including a cell of one or more tissues, as desired (e.g., pancreatic epithelial cells). In general, an array of probes that is "representative" of a genome will identify at least about 10% of the expressed nucleic acid molecules in a cell, generally at least about 20% or 40%, usually about 50% to 70%, typically at least about 80% or 90%, and particularly 95% to 99% or more of the expressed nucleic acid molecules of a cell or organism. It should be recognized that the greater the representation, the more likely that a method of the invention can identify all genes that are epigenetically silenced in a cancer. Arrays containing nucleotide sequences representative of specified genomes can be prepared using well known methods, or obtained from a commercial source (e.g., Invitrogen Corp.; Affymetrix), as exemplified by a Human Genome U133A chip (Affymetrix, Santa Clara, Calif.) used in the present studies.

The agent that reactivates expression of epigenetically silenced genes can be a methyltransferase inhibitor (e.g., 5 aza 2' deoxycytidine; 5Aza-dC), a histone deacetylase inhibitor (e.g., trichostatin A; TSA), or a combination of agents such as a combination of 5Aza-dC and TSA. RNA can be isolated from cells such as cancer cells treated with such an agent or agent, and the RNA, or a cDNA product of the RNA can be contacted with RNA molecules from corresponding cells (e.g., cancer cells) that were not treated with the agent(s) under conditions such that RNA (or cDNA) expressed only in the treated cells can be isolated, thus obtaining nucleic acid subtraction products. Methods for performing a nucleic acid subtraction reaction are well known (Hedrick et al., Nature 308:149-155, 1984, which is incorporated herein by reference), and kits for performing such methods are available from commercial sources (e.g., Gibco/BRL).

In another embodiment, the methods of the invention identify potential targets for aberrant methylation in pancreatic cancer by analyzing gene expression profiles of cancer cells after exposure to 5Aza-dC and/or TSA. This embodiment includes, in part, a comparison of the methylation status of a gene in a test cell or sample with the methylation status of a corresponding gene in a corresponding cell exhibiting regulated growth. As used herein, the term "corresponding" means a reference material, with which a test material is being compared. Generally, the reference material provides a control or standard with which the test material is compared. For example, reference to a corresponding unmethylated SFRP gene, with respect to an SFRP gene being examined for methylation status, means that the unmethylated SFRP gene is the same type of gene as the a SFRP gene being examined for methylation status, e.g., the test gene and the corresponding unmethylated gene are both human a SFRP1 genes. Reference to a corresponding cell exhibiting regulated growth, with respect to a test cell, generally refers to a normal cell, i.e., a cell that has a cell cycle and growth pattern characteristic of a population of such cells in a healthy individual, for example, a normal pancreatic epithelial cell where the test cell being examined is suspected of being a pancreatic cancer cell.

A test cell examined according to a method of the invention also can be a primary cell that has been obtained from a subject and placed in culture, for example, for the purpose of establishing a primary cell culture that exhibits substantially the same growth characteristics as the cells from which the culture was established, or for the purpose of treating and/or expanding the cells for readministration to the subject. For example, pancreatic ductal epithelial cells can be obtained from a cancer patient suffering from pancreatic cancer, wherein the cells exhibit methylation silenced expression of one or more genes associated with the cancer. The cells can be treated in culture using one or more agents to be tested for an ability to restore expression of the silenced gene(s), thus providing a means to identify an agent that can be useful for treating the cancer patient, or another patient having a pancreatic cancer characterized by methylation silencing of one or more of the same genes.

A test cell can be obtained from a subject in any way typically used in clinical setting for obtaining a sample containing the cells. For example, the test cells (or a sample comprising the test cells) can be obtained by a biopsy procedure such as needle biopsy of an organ or tissue containing the cells to be tested. As such, the test cells can be obtained from a gastrointestinal tract sample (e.g., a biopsy of a polyp), a liver sample, a pancreatic tissue sample, a bone marrow sample, a skin sample, a lymph node sample, a kidney sample, a lung sample, a muscle sample, a bone sample, a brain sample, or the like. The test cell also can be a component of a biological fluid, for example, blood, lymph, cerebrospinal fluid, pancreatic juice, saliva, sputum, stool, urine, or ejaculate. If appropriate, the test cells also can be obtained by lavage, for example, for obtaining test cells from the colon, uterus, abdominal cavity, or the like, or using an aspiration procedure, for example, for obtaining a bone marrow sample.

Where the epigenetic silencing includes methylation silencing, the method for identifying a cell that exhibits or is predisposed to exhibiting unregulated growth is performed by detecting methylation of one or more target genes in the cell. Methylation of a CpG dinucleotide in a CpG island of a gene can be detected using any of various well known methods for detecting CpG methylation of a nucleic acid molecule. Such methods include contacting the gene with one or a series of chemical reagents that selectively modify either unmethylated cytosine residues or methylated cytosine residues, but not both, such that the presence or absence of the modification can be detected; contacting the gene sequence with a methylation sensitive restriction endonuclease, which has a recognition site that includes a CpG dinucleotide, and that cleaves a recognition site either having a methylated cytosine residue of the CpG or lacking a methylated cytosine residue of the CpG, but not both, such that the presence or absence of cleavage of the sequence can be detected; or contacting a nucleic acid molecule comprising the gene with an oligonucleotide probe, primer, or amplification primer pair that selectively hybridizes to the gene sequence and allows a determination to made as to whether the CpG methylation is present. Examples of such methods are provided herein, and modifications and variations on such methods are well known in the art.

Methylation of a target gene can be detected, for example, by contacting a region comprising a 5' regulatory region of a nucleic acid molecule comprising the gene with a methylation sensitive restriction endonuclease, which cleaves a recognition site in the 5' regulatory region comprising a methylated cytosine residue of a CpG dinucleotide, whereby cleavage of the nucleic acid molecule is indicative of methylation and, therefore, methylation silencing of the gene of the test cell. Methylation sensitive restriction endonucleases are well known and include, for example, Acc III, Ban I, BstN I, Msp I, and Xma I. Alternatively, or in addition, methylation silencing can be detected by contacting a region comprising a 5' regulatory region of a nucleic acid molecule comprising the gene with a methylation sensitive restriction endonuclease, which cleaves a recognition site in the 5' regulatory region comprising a methylated cytosine residue of a CpG dinucleotide, provided the cytosine residue of the CpG dinucleotide is unmethylated, whereby a lack of cleavage of the nucleic acid molecule is indicative of methylation silencing of the gene of the test cell. Such methylation sensitive restriction endonucleases are exemplified by Acc II, Ava I, BssH II, BstU I, Hpa II, and Not I.

The presence or absence of cleavage of a nucleic acid molecule comprising a target gene sequence by a methylation sensitive restriction endonuclease can be identified using any method useful for detecting the length or continuity of a polynucleotide sequence. For example, cleavage of the target gene sequence can be detected by Southern blot analysis, which allows mapping of the cleavage site, or using any other electrophoretic method or chromatographic method that separates nucleic acid molecules on the basis of relative size, charge, or a combination thereof. Cleavage of a target gene also can be detected using an oligonucleotide ligation assay, wherein, following contact with the restriction endonuclease, a first oligonucleotide that selectively hybridizes upstream of and adjacent to a restriction endonuclease cleavage site and a second oligonucleotide that selectively hybridizes downstream of and adjacent to the cleavage site are contacted with the target gene sequence, and further contacted with a ligase such that, in the absence of cleavage the oligonucleotides are adjacent to each other and can be ligated together, whereas, in the absence of cleavage, ligation does not occur. By determining the size or other relevant parameter of the oligonucleotides following the ligation reaction, ligated oligonucleotides can be distinguished from unligated oligonucleotides, thereby providing an indication of restriction endonuclease activity.

Methylation silencing of a gene also can be detected by contacting a 5' regulatory region of the nucleic acid molecule comprising the gene of the test cell with a chemical reagent that selectively modifies either an unmethylated cytosine residue or a methylated cytosine residue, and detecting a product generated due to the contacting, wherein the product is indicative of methylation of a cytosine residue in a CpG dinucleotide of the gene, thereby detecting methylation silencing of the gene of the test cell. For example, the product can be detected using an electrophoresis method, a chromatography method, a mass spectrometry method, or a combination of such methods.

In one aspect of the present invention, a nucleic acid molecule comprising the target gene is contacted with a chemical reagent comprising bisulfite ions, for example, sodium bisulfite, which converts unmethylated cytosine residues to bisulfite modified cytosine residues, then the bisulfite ion treated gene sequence is exposed to alkaline conditions, which convert bisulfite modified cytosine residues to uracil residues. Sodium bisulfite reacts readily with the 5,6 double bond of cytosine (but poorly with methylated cytosine) to form a sulfonated cytosine reaction intermediate that is susceptible to deamination, giving rise to a sulfonated uracil. As such, the sulfonate group can be removed by exposure to alkaline conditions, resulting in the formation of uracil. The DNA then can amplified, for example, by PCR, and sequenced to determine the methylation status of all CpG sites. Uracil is recognized as a thymine by Taq polymerase and, upon PCR, the resultant product contains cytosine only at the position where 5 methylcytosine was present in the starting template DNA. By comparing the amount or distribution of uracil residues in the bisulfite ion treated gene sequence of the test cell with a similarly treated corresponding unmethylated gene sequence, detection of a decrease in the amount or distribution of uracil residues in the gene from the test cell is indicative of methylation of cytosine residues in CpG dinucleotides in the target gene of the test cell. The amount or distribution of uracil residues also can be detected by contacting the bisulfite ion treated target gene sequence, following exposure to alkaline conditions, with an oligonucleotide that selectively hybridizes to a nucleotide sequence of the target gene that either contains uracil residues or that lacks uracil residues, but not both, and detecting selective hybridization (or the absence thereof) of the oligonucleotide.

As used herein, the term "selective hybridization" or "selectively hybridize" or "specific hybridization" refers to an interaction of two nucleic acid molecules that occurs and is stable under moderately stringent or highly stringent conditions. As such, selective hybridization preferentially occurs, for example, between an oligonucleotide and a target nucleic acid molecule, and not substantially between the oligonucleotide and a nucleic acid molecule other than the target nucleic acid molecule, including not with nucleic acid molecules encoding related but different members of a gene family. Generally, an oligonucleotide useful as a probe or primer that selectively hybridizes to a target nucleic acid molecule is at least about 12 to 15 nucleotides in length, generally at least about 18 to 20 nucleotides in length, usually at least about 21 to 25 nucleotides in length, and particularly about 26 to 35 nucleotides in length or. Examples of oligonucleotides useful in practicing the methods of the invention are disclosed herein in Table 4.

Conditions that allow for selective hybridization can be determined empirically, or can be estimated based, for example, on the relative GC:AT (or GC:AU) content of the hybridizing oligonucleotide and the target nucleic acid molecule, the length of the hybridizing oligonucleotide, and the number, if any, of mismatches between the oligonucleotide and target sequence to which it is to hybridize (see, for example, Sambrook et al., "Molecular Cloning: A laboratory manual (Cold Spring Harbor Laboratory Press 1989)). As such, the conditions used to achieve a particular level of stringency will vary, depending on the nature of the hybridizing nucleic acid molecules. An additional consideration is whether one of the nucleic acids is immobilized, for example, on a filter. An example of progressively higher stringency conditions is as follows: 2×SSC/0.1% SDS at about room temperature (hybridization conditions); 0.2×SSC/0.1% SDS at about room temperature (low stringency conditions); 0.2× SSC/0.1% SDS at about 42° C. (moderate stringency conditions); and 0.1×SSC at about 62° C. (high stringency conditions). Hybridization and/or washing can be carried out using only one of these conditions, for example, high stringency conditions, or each of the conditions can be used, for example, for 10 to 15 minutes each, in the order listed above, repeating any or all of the steps listed.

Selective hybridization of an oligonucleotide with a target gene (e.g., a gene as listed in Tables 1-3) can be detected, for example, by performing the method using an oligonucleotide that includes a detectable label. The detectable label can be any molecule that conveniently can be linked to the oligonucleotide and detected using readily available equipment. For example, the detectable label can be a fluorescent compound such a Cy3, Cy5, Fam, fluorescein, rhodamine, or a green fluorescent protein or enhanced or modified form thereof; a radionuclide such as sulfur-35, technicium-99, phosphorus-32, tritium or iodine 125; a paramagnetic spin label such as carbon-13, Gd-157, Mn-55, Dy-162, Cr 52, or Fe 56; a luminescent compound such as an aequorin; a chemi-luminescent compound; a metal chelate; an enzyme such as luciferase or J-galactosidase, or a substrate for an enzyme; or a receptor or a ligand for a receptor, for example, biotin. The means for detecting the detectable label will be selected based on the characteristics of the label, as will the means for linking the label to an oligonucleotide (see, for example, Hermanson, "Bioconjugate Techniques" (Academic Press 1996), which is incorporated herein by reference).

Selective hybridization also can be detected, for example, by utilizing the oligonucleotide as a substrate for a primer extension reaction, further contacting the sample with deoxyribonucleotides (dNTPs), including, if desired, a detectable dNTP (e.g., a fluorescently labeled dNTP, a digoxigenin labeled dNTP, or a biotin labeled dNTP), and a DNA dependent DNA polymerase under conditions sufficient for the primer extension reaction to proceed, and detecting a product of the primer extension reaction. Conditions for performing a primer extension reaction are well known in the art (see, for example, Sambrook et al., supra, 1989).

The amount or distribution of uracil residues in a bisulfite ion treated nucleic acid molecule comprising a target gene sequence following exposure to alkaline conditions also can be detected using an amplification reaction such as PCR. An amplification reaction is performed under conditions that allow selective hybridization of the forward and reverse primers of an amplification primer pair to the target nucleic acid molecule. Generally, the reaction is performed in a buffered aqueous solution, at about pH 7-9, usually about pH 8. In addition, the reaction generally is performed in a molar excess of primers to target nucleic acid molecule, for example, at a ratio of about 100:1 prime:genomic DNA. Where the amount of the target nucleic acid molecule in a sample is not known, for example, in a diagnostic procedure using a biological sample, a range of primer amounts can be used in samples run in parallel, although generally even the addition of a small amount of primers will result in a sufficient molar excess such that the amplification reaction can proceed.

The deoxyribonucleoside triphosphates, dATP, dCTP, dGTP, and dTTP, can be added to the synthesis mixture either separately or as a mixture, which can further include the primers, in adequate amounts and the resulting solution is heated to about 90°-100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction, generally a polymerase, and the reaction is allowed to occur under conditions as disclosed herein (see Example 1) or otherwise known in the art. Where the polymerase is heat stable, it can be added together with the other reagents. The polymerase can be any enzyme useful for directing the synthesis of primer extension products, including, for example, E. coli DNA polymerase I, Klenow fragment of E. coli DNA polymerase I, T4 DNA polymerase, other available DNA polymerases, polymerase muteins, reverse transcriptase, and other enzymes, including heat-stable enzymes, as are well known in the art and commercially available. The amplification products can be identified as methylated or non-methylated by a sequencing method, oligomer restriction (Saiki et al., BioTechnology 3:1008-1012, 1985), allele-specific oligonucleotide probe analysis (Conner et al., Proc. Natl. Acad. Sci. USA 80:278, 1983), oligonucleotide ligation assays (Landegren et al., Science 241:1077, 1988), and the like (see, also, Landegren et al., Science 242:229-237, 1988).

In one embodiment, a methylation-specific amplification reaction such as methylation-specific PCR (MSP) is used alone, or in combination with bisulfite treatment, to detect the methylation status, of a nucleic acid molecule (see U.S. Pat. Nos. 6,265,171; 6,200,756; and 6,017,704, each of which is incorporated herein by reference; see, also, Example 1). MSP is a particularly sensitive method that allows detection of low numbers of methylated alleles and the use of small amounts of a nucleic acid sample, including paraffin-embedded materials, and also can be conveniently adapted to a multiplex analysis, including, for example, simultaneous detection of unmethylated and methylated products in a single sample, thus providing an internal control.

The amplification primer pairs used in an MSP reaction are designed to specifically distinguish between bisulfite untreated or unmodified DNA, and methylated and unmethylated DNA. MSP primer pairs for unmethylated DNA (unmethylation specific primer pairs) generally have a thymidine residue in the 3' CpG pair to distinguish it from the cytosine residue retained in methylated DNA, and the complement is designed for the antisense primer. MSP primer pairs usually contain relatively few cytosine or guanine residues in the sequence because cytosine is absent in the sense (forward) primer and the guanine is absent in the antisense (reverse) primer; cytosine becomes modified to uracil, which is amplified as thymidine in the amplification product. MSP unmethylation (MSP(U)) specific primer pairs and MSP methylation (MSP(M)) specific are exemplified in Table 4. For example, amplification primer pairs useful for such a method include, for example, methylation specific primer pairs as set forth in SEQ ID NO:3 and 4 for cadherin3 (CDH3); SEQ ID NOS:7 and 8 for reprimo; SEQ ID NOS:11 and 12 for claudin 5 (CLDN5); SEQ ID NOS:15 and 16 for death receptor 3 (DR3); SEQ ID NOS:19 and 20 for forkhead box E1 (FOXE1); SEQ ID NOS:23 and 24 for leucine zipper down regulated in cancer 1 (LDOC1); SEQ ID NOS:27 and 28 for LIM homeobox protein 1 (LHX1); SEQ ID NOS:31 and 32 for neurofilament heavy polypeptide (NEFH); SEQ ID NOS: 35 and 36 for neuronal pentraxin II (NPTX2); SEQ ID NOS: 39 and 40 for p53-induced protein (PIG11); SEQ ID NOS:43 and 44 for secreted apoptosis related protein 2 (SARP2); SEQ ID NOS:47 and 48 for suppression of tumorigenicity 14 (ST14); SEQ ID NOS:51 and 52 for SWI/SNF-related gene (SMARCA1); SEQ ID NOS:55 and 56 for tight junction protein 2 (TJP2); SEQ ID NOS:59 and 60 for ubiquitin carboxyl-terminal esteraseL1 (UCHL1); or SEQ ID NOS:63 and 64 for wingless-type MMTV integration site family, member 7A (WNT7A). Amplification primer pairs useful for such a method include, for example, unmetnylation specific primer pairs as set form in SEQ ID NO:1 and 2 for cadherin3 (CDH3); SEQ ID NOS:5 and 6 for reprimo; SEQ ID NOS:9 and 10 for claudin 5 (CLDN5); SEQ ID NOS:13 and 14 for death receptor 3 (DR3); SEQ ID NOS:17 and 18 for forkhead box E1 (FOXE1), SEQ ID NOS:21 and 22 for leucine zipper down-regulated in cancer 1 (LDOCJ); SEQ ID NOS:25 and 26 for LIM homeobox protein 1 (LHX1); SEQ ID NOS:29 and 30 for neurofilament heavy polypeptide (NEFH); SEQ ID NOS:33 and 34 for neuronal pentraxin II (NPTX2); SEQ ID NOS:37 and 38 for p53-induced protein (PIG11); SEQ ID NOS:41 and 42 for secreted apoptosis related protein 2 (SARP2); SEQ ID NOS:45 and 46 for suppression of tumorigenicity 14 (ST14); SEQ ID NOS:49 and 50 for SWI/SNF-related gene (SMARCA1); SEQ ID NOS:53 and 54 for tight junction protein 2 (TJP2); SEQ ID NOS:57 and 58 for ubiquitin carboxyl-terminal esteraseL1 (UCHL1); or SEQ ID NOS:61 and 62 for wingless-type MMTV integration site family, member 7A (WNT7A).

In view of the exemplified methylation-specific and unmethylation-specific primer pairs, and the availability of nucleotide sequences comprising portions of target genes such as those listed in Tables 1-3, it will be recognized that additional methylation-specific and unmethylation-specific primer pairs useful for amplification of a methylated or an unmethylated gene as listed in Tables 1-3 or other identified target genes, as well as for family members related to the listed genes readily can be made.

Accordingly, in one aspect, MSP is used for detecting the amount or distribution of uracil residues in a bisulfite ion treated target genes following alkaline treatment Such a method can be performed by contacting the gene sequence with a first amplification primer pair and a second amplification primer pair under conditions suitable for amplification, wherein the first amplification primer pair comprises a forward primer and a reverse primer, and at least one primer of the first primer pair comprises an oligonucleotide mat selectively hybridizes to a nucleotide sequence of the target gene that contains uracil residues, and wherein the second amplification primer pair comprises a forward primer and a reverse primer, and both primers of the second primer pair selectively hybridize to a target gene containing cytosine residues, but not to a target gene sequence containing uracil residues, and wherein an amplification product, if any, generated by the first primer pair has a first length, and an amplification product, if any, generated by the second primer pair has a second length, which is different from the first length, whereby the length of the amplification products is indicative of the amount or distribution of uracil residues and, therefore, of methylation of cytosine residues in CpG dinucleotides in the target gene of the test cell.

The amount or distribution of uracil residues also can be detected by contacting the 5' regulatory region of the gene with a first amplification primer pair and a second amplification primer pair under conditions suitable for amplification, wherein the first amplification primer pair comprises a forward primer and a reverse primer, wherein at least one primer of the first primer pair comprises an oligonucleotide that selectively hybridizes to a nucleotide sequence of the 5' regulatory region of the gene containing uracil residues, and wherein the second amplification primer pair comprises a forward primer and a reverse primer, wherein both primers of the second primer pair selectively hybridize to a nucleotide sequence of the 5' regulatory region of the gene containing cytosine residues, but not to a corresponding nucleotide sequence of the 5' regulatory region of the gene containing uracil residues, and wherein an amplification product, if any, generated by the first primer pair has a first length, and wherein an amplification product, if any, generated by the second primer pair has a second length, which is different from the first length, whereby the length of the amplification products is indicative of uracil residues and, therefore, methylation of cytosine residues in CpG dinucleotides in the 5' regulatory region of the gene, thereby detecting methylation silencing of the gene of the test cell.

Methylation silencing of a gene in a cell exhibiting or suspected of exhibiting unregulated growth (e.g., a gene associated with a cancer) also can be identified by contacting a test cell with a demethylating agent, and detecting increased expression of an RNA encoded by the gene as compared to a level of expression of the RNA in a test cell not contacted with a demethylating agent. Such a method can further include detecting methylation, if any, of cytosine residues in a CpG dinucleotide in a CpG island of the 5' regulatory region of the gene in a corresponding cell exhibiting regulated growth, or an extract of the corresponding cell The demethylating agent can be a methyltransferase inhibitor such as DAC. Increased expression of an RNA can be detected using any method for detecting RNA, including, for example, northern blot analysis, a reverse transcription-polymerase chain reaction assay, or selective hybridization to an array of nucleotide sequences as disclosed herein. Accordingly, the methods of the invention can be performed in a high throughput format, wherein the test cell, or extract of the test cell, comprises one of a plurality of test cells, or extracts of the test cells, or a combination thereof; and each of the test cells, or extracts of the test cells, of the plurality is the same or different, or a combination thereof.

In adapting the methods of the invention to a high throughput format, the test cells, or extracts of the test cell, can be arranged in an array, which can be an addressable array, on a solid support such as a microchip, a glass slide, or a bead, and the cells (or extracts) can be contacted serially or in parallel with an oligonucleotide probe or primer (or primer pair) as disclosed herein. Samples arranged in an array or other reproducible pattern can be assigned an address (i.e., a position on the array), thus facilitating identification of the source of the sample. An additional advantage of arranging the samples in an array, particularly an addressable array, is that an automated system can be used for adding or removing reagents from one or more of the samples at various times, or for adding different reagents to particular samples. In addition to the convenience of examining multiple samples at the same time, such high throughput assays provide a means for examining duplicate, triplicate, or more aliquots of a single sample, thus increasing the validity of the results obtained, and for examining control samples under the same conditions as the test samples, thus providing an internal standard for comparing results from different assays. Conveniently, cells or extracts at a position in the array can be contacted with two or more oligonucleotide probes or primers (or primer pairs), wherein the oligonucleotides are differentially labeled or comprise a reaction that generates distinguishable products, thus providing a means for performing a multiplex assay. Such assays can allow the examination of one or more, particularly 2, 3, 4, 5, 10, 15, 20, or more genes to identity epigenetically silenced genes in a test cell.

The present invention also provides oligonucleotides, which can be useful as probes or primers for identifying an epigenetic silenced gene (or the absence thereof). As used herein, the term "oligonucleotide", "polynucleotide", or "nucleic acid molecule" is used broadly to mean a sequence of two or more deoxyribonucleotides or ribonucleotides that are linked together by a phosphodiester bond. An "isolated polynucleotide" is a polynucleotide that is not immediately contiguous with both of the coding sequences with which it is immediately contiguous (one on the 5' end and one on the 3' end) in the naturally occurring genome of the organism from which it is derived. Thus, an isolated polynucleotide may include a coding region with its associated regulatory sequences. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. Specifically, methylated forms of nucleotides in a polynucleotide sequence are also included. The term includes single and double forms of DNA.

The term "gene" also is used herein to refer to a polynucleotide sequence contained in a genome. It should be recognized, however, that a nucleic acid molecule comprising a portion of a gene can be isolated from a cell or can be examined as genomic DNA, for example, by a hybridization reaction or a PCR reaction. Thus, while in a genome, it may not always be clear as to a specific nucleotide position where a gene begins or ends, for purposes of the present invention, a gene is considered to be a discrete nucleic acid molecule that includes at least the nucleotide sequence set forth in the GenBank Accession Numbers shown in Tables 1-3 for various genes identified and/or examined herein.

As will be understood by those of skill in the art, when the sequence is RNA, the deoxynucleotides A, G, C, and T of DNA are replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the polypeptides.

The nucleic acid sequence includes the disclosed sequence and sequences that encode conservative variations of the polypeptides encoded by polynucleotides provided herein. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Nucleic acid sequences of the invention can be expressed in vitro by DNA transfer into a suitable host cell. "Host cells" are cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cells" is used. Methods of stable transfer, meaning that the foreign DNA is continuously maintained in the host, are known in the art.

In one aspect, the nucleic acid sequences may be inserted into an expression vector. The term "expression vector" refers to a plasmid, virus or other vehicle known in the art that has been manipulated by insertion or incorporation of the sequence of interest genetic sequences. Polynucleotide sequence which encode sequence of interest can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the regulatory or expression control sequences. As used herein, the terms "regulatory sequences" and "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The terms "regulatory sequences" and "expression control sequences" are intended to included, at a minimum, components whose presence can influence expression, and can also include additional components whose presence is advantageous, for example, leader sequences and fusion partner sequences. An example of an expression control sequence includes a promoter.

A "promoter" is a minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see, e.g., Bitter et al., Methods in Enzymology 153:516-544, 1987). For example, when cloning in bacterial systems, inducible promoters such as pL of bacteriophage plac, ptrpj ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In the present invention, the polynucleotide sequences may be inserted into an expression vector which contains a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., Gene 56:125, 1987), the pMSXND expression vector for expression in mammalian cells (Lee and Nathans, J. Biol. Chem. 263:3521, 1988) and baculovirus-derived vectors for expression in insect cells. The DNA segment can be present in the vector operably linked to regulatory elements, for example, a promoter (e.g., T7, metallothionein I, or polyhedron promoters).

Polynucleotide sequences of the invention can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

"Transformation" means a genetic change induced in a cell following incorporation of new DNA (i.e., DNA exogenous to the cell). Where the cell is a mammalian cell, the genetic change is generally achieved by introduction of the DNA into the genome of the cell (i.e., stable).

Thus, a "transformed cell" is a cell into which (or into an ancestor of which) has been introduced, by means of recombinant DNA techniques, a DNA molecule encoding sequence of interest Transformation of a host cell with recombinant DNA may be carried out by conventional techniques as are well known to those skilled in the art. Where the host is prokaryotic, such as $E.$ $coli$, competent cells which are capable of DNA uptake can be prepared from cells harvested after exponential growth phase and subsequently treated by the $CaC_2$ method using procedures well known in the art Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the sequence of interest, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

In one embodiment, the invention provides substantially purified polypeptides. The term "substantially purified" as used herein refers to a polypeptide which is substantially free of other proteins, lipids, carbohydrates or other materials with which it is naturally associated. One skilled in the art can purify a polypeptide sequence using standard techniques for protein purification. The substantially pure polypeptide will yield a single major band on a non-reducing polyacrylamide gel. The purity of the polypeptide can also be determined by amino-terminal amino acid sequence analysis.

Minor modifications of the primary amino acid sequences may result in proteins which have substantially equivalent activity as compared to the unmodified counterpart polypeptide described herein. Such modifications may be deliberate, as by site-directed mutagenesis, or may be spontaneous. All of the polypeptides produced by these modifications are included herein as long as the biological activity still exists.

The polypeptides of the invention also include dominant negative forms of the invention polypeptide which do not have the biological activity of invention polypeptide sequence. A "dominant negative form" of invention is a polypeptide that is structurally similar to the invention polypeptide but does not have wild-type invention function. For example, a dominant-negative invention polypeptide may interfere with wild-type invention function by binding to, or otherwise sequestering, regulating agents, such as upstream or downstream components, that normally interact functionally with the invention polypeptide.

Due to the clear correlation between methylation of CpG islands and cellular proliferative disorders, in another embodiment of the present invention, there are provided methods for detecting a cellular proliferative disorder in a subject having or at risk for the cellular proliferative disorder. The method includes assaying, in nucleic acid-containing specimen taken from the subject, the methylation state of a gene or its associated regulatory regions, wherein the expression state of the gene or its associated regulatory regions is associated with the presence of the cellular proliferative disorder, and identifying as having a cellular proliferative disorder a subject that has aberrant methylation of regions of the gene. The method provides for detecting a cellular proliferative disorder in a subject having or at risk for the cellular proliferative disorder by identifying aberrantly methylation of regions of a gene when compared to the same regions of the gene in a subject not having the cellular proliferative disorder.

The aberrant methylation comprises hypermethylated CpG rich regions (i.e., islands). In one aspect of the present invention, the CpG rich regions are associated with the invention genes, and affect the expression thereof in a methylation state-dependent manner.

A "cell proliferative disorder" or "cellular proliferative disorder" is any disorder in which the proliferative capabilities of the affected cells is different from the normal proliferative capabilities of unaffected cells. An example of a cell proliferative disorder is neoplasia. Malignant cells (i.e., cancer) develop as a result of a multistep process. Specific, non-limiting examples of cell proliferative disorders associated with increased methylation of CpG-islands are low grade astrocytoma, anaplastic astrocytoma, glioblastoma, medulloblastoma, gastric cancer, colorectal cancer, colorectal adenoma, acute myelogenous leukemia, lung cancer, renal cancer, pancreatic cancer, leukemia, breast cancer, prostate cancer, endometrial cancer and neuroblastoma. The illustrative example of the present invention is pancreatic cancer.

A cell proliferative disorder as described herein may be a neoplasm. Such neoplasms are either benign or malignant. The term "neoplasm" refers to a new, abnormal growth of cells or a growth of abnormal cells that reproduce taster than normal. A neoplasm creates an unstructured mass (a tumor) which can be either benign or malignant For example, the neoplasm may be a head, neck, lung, esophageal, stomach, small bowel, colon, bladder, kidney, or cervical neoplasm. The term "benign" refers to a tumor that is noncancerous, e.g. its cells do not proliferate or invade surrounding tissues. The term "malignant" refers to a tumor that is metastastic or no longer under normal cellular growth control.

A cell proliferative disorder may be an age-associated disorder. Examples of age-associated disorders which are cell proliferative disorders include colon cancer, lung cancer, breast cancer, prostate cancer, and melanoma, amongst others.

A "nucleic acid containing specimen" includes any type of material containing a nucleic acid to be subject to invention methods. The nucleic acid may be contained in a biological sample. Such samples include but are not limited to any bodily fluid, such as a serum, urine, saliva, blood, cerebrospinal fluid, pleural fluid, ascites fluid, sputum, stool, or a biopsy sample.

Samples or specimens include any CpG-rich DNA sequence, whatever the origin, as long as the sequence is detectably present in a sample. While routine diagnostic tests may not be able to identity cancer cells in these samples, the method of the present invention identifies neoplastic cells derived from the primary tumor or from a metastases. The method includes non-invasive sampling (e.g., bodily fluid) as well as invasive sampling (e.g., biopsy). The sample of DNA of the subject may be serum, plasma, lymphocytes, urine, sputum, bile, stool, cervical tissue, saliva, tears, pancreatic juice, duodenal juice, cerebral spinal fluid, regional lymph node, histopathologic margins, and any bodily fluid that drains a body cavity or organ. Therefore, the method provides for the non-invasive detection of various tumor types including head and neck cancer, lung cancer, esophageal cancer, stomach cancer, small bowel cancer, colon cancer, bladder cancer, kidney cancers, pancreatic cancers, cervical cancer and any other organ type that has a draining fluid accessible to analysis. For example, neoplasia of regional lymph nodes associated with a primary mammary tumor can be detected using the method of the invention. Regional lymph nodes for head and neck carcinomas include cervical lymph nodes, prelaryngeal lymph nodes, pulmonary juxta-esophageal lymph nodes and submandibular lymph nodes. Regional lymph nodes for mammary tissue carcinomas include the axillary and intercostal nodes. Samples also include urine DNA for bladder cancer or plasma or saliva DNA for head and neck cancer patients.

Any nucleic acid sample, in purified or nonpurified form, can be utilized as the starting nucleic acid or acids in accordance with the present invention, provided it contains, or is suspected of containing, a nucleic acid sequence containing a target locus (e.g., CpG-containing nucleic acid). In general, the CpG-containing nucleic acid is DNA. However, invention methods may employ, for example, samples that contain DNA, or DNA and RNA, including messenger RNA, wherein DNA or RNA may be single stranded or double stranded, or a DNA-RNA hybrid may be included in the sample. A mixture of nucleic acids may also be employed. The specific nucleic acid sequence to be detected may be a fraction of a larger molecule or can be present initially as a discrete molecule, so that the specific sequence constitutes the entire nucleic acid. It is not necessary that the sequence to be studied be present initially in a pure form; the nucleic acid may be a minor fraction of a complex mixture, such as contained in whole human DNA. The nucleic acid-containing sample used for detection of methylated CpG may be from any source including, but not limited to, brain, colon, urogenital, lung, renal, pancreas, liver, esophagus, stomach, hematopoietic, breast, thymus, testis, ovarian, and uterine tissue, and may be extracted by a variety of techniques such as that described by Maniatis, et al. (*Molecular Cloning: a Laboratory Manual*, Cold Spring Harbor, N.Y., pp 280, 281, 1982).

The nucleic acid of interest can be any nucleic acid where it is desirable to detect the presence of a differentially methylated CpG island. The CpG island comprises a CpG island located in a gene or regulatory region for a gene. A "CpG island" is a CpG rich region of a nucleic acid sequence. The nucleic acid sequence may include, for example, MICP 1-42. However, any gene or nucleic acid sequence of interest containing a CpG sequence can provide diagnostic information (i.e., via its methylation state) using invention methods.

Moreover, these markers can also be multiplexed in a single amplification reaction to generate a low cost, reliable cancer screening test for many cancers simultaneously.

A combination of DNA markers for CpG-rich regions of nucleic acid may be amplified in a single amplification reaction. The markers are multiplexed in a single amplification reaction, for example, by combining primers for more man one locus. For example, DNA from a urine sample can be amplified with three different randomly labeled primer sets, such as those used for the amplification of the MICP38-42 loci, in the same amplification reaction. The reaction products are separated on a denaturing polyacrylamide gel, for example, and then exposed to film for visualization and analysis. By analyzing a panel of markers, there is a greater probability of producing a more useful methylation profile for a subject.

If the sample is impure (e.g., plasma, serum, stool, ejaculate, sputum, saliva, cerebrospinal fluid, or blood or a sample embedded in paraffin), it may be treated before amplification with a reagent effective for lysing the cells contained in the fluids, tissues, or animal cell membranes of the sample, and for exposing the nucleic acid(s) contained therein. Methods for purifying or partially purifying nucleic acid from a sample are well known in the art (e.g., Sambrook et al., *Molecular Cloning; a Laboratory Manual*, Cold Spring Harbor Press, 1989, herein incorporated by reference).

In order to detect a differential methylation state for a gene or CpG-containing region of interest, invention methods include any means known in the art for detecting such differential methylation. For example, detecting the differential methylation may include contacting the nucleic acid-containing specimen with an agent that modifies unmethylated cytosine, amplifying a CpG-containing nucleic acid in the specimen by means of CpG-specific oligonucleotide primers, wherein the oligonucleotide primers distinguish between modified methylated and nonmethylated nucleic acid, and detecting the methylated nucleic acid based on the presence or absence of amplification products produced in the amplifying step. This embodiment includes the PCR-based methods described in U.S. Pat. No. 5,786,146, incorporated herein in its entirety.

For the first time, the methylation state of a number of genes has been correlated with cell proliferative disorders, and more specifically pancreatic cancers. Examples of such genes and their NCBI accession numbers, including the location of the clone, are set out in Tables 1-3.

In another embodiment, detection of differential methylation is accomplished by contacting a nucleic acid sample suspected of comprising a CpG-containing nucleic acid with a methylation sensitive restriction endonuclease that cleaves only unmethylated CpG sites under conditions and for a time to allow cleavage of unmethylated nucleic acid. The sample is further contacted with an isoschizomer of the methylation sensitive restriction endonuclease, mat cleaves both methylated and unmethylated CpG-sites, under conditions and for a time to allow cleavage of methylated nucleic acid. Oligonucleotides are added to the nucleic acid sample under conditions and for a time to allow ligation of the oligonucleotides to nucleic acid cleaved by the restriction endonuclease, and the digested nucleic acid is amplified by conventional methods such as PCR wherein primers complementary to the oligonucleotides are employed. Following identification, the methylated CpG-containing nucleic acid can be cloned, using method well known to one of skill in the art (see Sambrook et al., *Molecular Cloning: a Laboratory Manual*, Cold Spring Harbor Press, 1989).

As used herein, a "methylation sensitive restriction endonuclease" is a restriction endonuclease that includes CG as part of its recognition site and has altered activity when the C is methylated as compared to when the C is not methylated. Preferably, the methylation sensitive restriction endonuclease has inhibited activity when the C is methylated (e.g., SmaI). Specific non-limiting examples of a methylation sensitive restriction endonucleases include Sma I, BssHII, or HpaII. Such enzymes can be used alone or in combination. Other methylation sensitive restriction endonucleases will be known to those of skill in the art and include, but are not limited to SacII, EagI, and BstUI, for example. An "isoschizomer" of a methylation sensitive restriction endonuclease is a restriction endonuclease which recognizes the same recognition site as a methylation sensitive restriction endonuclease but which cleaves both methylated and unmethylated CGs. One of skill in the art can readily determine appropriate conditions for a restriction endonuclease to cleave a nucleic acid (see Sambrook et al, *Molecular Cloning: a Laboratory Manual*, Cold Spring Harbor Press, 1989). Without being bound by theory, actively transcribed genes generally contain fewer methylated CGs than in other genes.

In one embodiment of the invention, a nucleic acid of interest is cleaved with a methylation sensitive endonuclease. In one aspect, cleavage with the methylation sensitive endonuclease creates a sufficient overhang on the nucleic acid of interest. Following cleavage with the isoschizomer, the cleavage product can still have a sufficient overhang. An "overhang" refers to nucleic acid having two strands wherein the strands end in such a manner that a few bases of one strand are not base paired to the other strand. A "sufficient overhang" refers to an overhang of sufficient length to allow specific hybridization of an oligonucleotide of interest. In one embodiment, a sufficient overhang is at least two bases in length. In another embodiment, the sufficient overhang is four or more bases in length. An overhang of a specific sequence on the nucleic acid of interest may be desired in order for an oligonucleotide of interest to hybridize. In this case, the isoschizomer can be used to create the overhang having the desired sequence on the nucleic acid of interest.

In another aspect of this embodiment, the cleavage with a methylation sensitive endonuclease results in a reaction product of the nucleic acid of interest that has a blunt end or an insufficient overhang. In this embodiment, an isoschizomer of the methylation sensitive restriction endonuclease can create a sufficient overhang on the nucleic acid of interest. "Blunt ends" refers to a flush ending of two stands, the sense stand and the antisense strand, of a nucleic acid.

Once a sufficient overhang is created on the nucleic acid of interest, an oligonucleotide is ligated to the nucleic acid cleaved of interest which has been cleaved by the methylation specific restriction endonuclease. "Ligation" is the attachment of two nucleic acid sequences by base pairing of substantially complementary sequences and/or by the formation of covalent bonds between two nucleic acid sequences. In one aspect of the present invention, an "oligonucleotide" is a nucleic acid sequence of about 2 up to about 40 bases in length. It is presently preferred that the oligonucleotide is from about 15 to 35 bases in length.

In one embodiment, an adaptor is utilized to create DNA ends of desired sequence and overhang. An "adaptor" is a double-stranded nucleic acid sequence with one end that has a sufficient single-stranded overhang at one or both ends such that the adaptor can be ligated by base-pairing to a sufficient overhang on a nucleic acid of interest that has been cleaved by a methylation sensitive restriction enzyme or an isoschizomer of a methylation sensitive restriction enzyme. Adaptors can be obtained commercially, or two oligonucleotides can be utilized to form an adaptor. Thus, in one embodiment, two oligonucleotides are used to form an adaptor; these oligonucleotides are substantially complementary over their entire sequence except for the region(s) at the 5' and/or 3' ends that will form a single stranded overhang. The single stranded overhang is complementary to an overhang on the nucleic acid cleaved by a methylation sensitive restriction enzyme or an isoschizomer of a methylation sensitive restriction enzyme, such that the overhang on the nucleic acid of interest will base pair with the 3' or 5' single stranded end of the adaptor under appropriate conditions. The conditions will vary depending on the sequence composition (GC vs AT), the length, and the type of nucleic acid (see Sambrook et al., *Molecular Cloning: a Laboratory Manual*, 2nd Ed.; Cold Spring Harbor Laboratory Press, Plainview, N.Y., 1998).

Following the ligation of the oligonucleotide, the nucleic acid of interest is amplified using a primer complementary to the oligonucleotide. Specifically, the term "primer" as used herein refers to a sequence comprising two or more deoxyribonucleotides or ribonucleotides, preferably more than three, and more preferably more than eight, wherein the sequence is capable of initiating synthesis of a primer extension product, which is substantially complementary to a nucleic acid such as an adaptor or a ligated oligonucleotide. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. In one embodiment, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12-20 or more nucleotides, although it may contain fewer nucleotides.

Primers of the invention are designed to be "substantially" complementary to each strand of the oligonucleotide to be amplified and include the appropriate G or C nucleotides as discussed above. This means that the primers must be sufficiently complementary to hybridize with their respective strands under conditions which allow the agent for polymerization to perform. In other words, the primers should have sufficient complementarity with a 5' and 3' oligonucleotide to hybridize therewith and permit amplification of CpG containing nucleic acid sequence.

Primers of the invention are employed in the amplification process which is an enzymatic chain reaction that produces exponential quantities of target locus relative to the number of reaction steps involved (e.g., polymerase chain reaction or PCR). Typically, one primer is complementary to the negative (−) strand of the locus and the other is complementary to the positive (+) strand. Annealing the primers to denatured nucleic acid followed by extension with an enzyme, such as the large fragment of DNA Polymerase I (Klenow) and nucleotides, results in newly synthesized + and − strands containing the target locus sequence. Because these newly synthesized sequences are also templates, repeated cycles of denaturing, primer annealing, and extension results in exponential production of the region (i.e., the target locus sequence) defined by the primer. The product of the chain reaction is a discrete nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, dietbylphos-phoramidites are used as starting materials and may be synthesized as described by Beaucage, et al. (Tetrahedron Letters, 22:1859-1862, 1981). One method for synthesizing oligonucleotides on a modified solid support is described in U.S. Pat. No. 4,458,066.

Where the CpG-containing nucleic acid sequence of interest contains two strands, it is necessary to separate the strands of the nucleic acid before it can be used as a template for the amplification process. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffman-Berling (CSH-Quantitative Biology, 43:63, 1978) and techniques for using RecA are reviewed in C. Redding (Ann. Rev. Genetics, 16:405-437, 1982).

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, generally at a pH of about 7-9. Preferably, a molar excess (for genomic nucleic acid, usually about 108:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands, a large molar excess is preferred to improve the efficiency of the process.

The deoxyribonucleoside triphosphates dATP, dCTP, dGTP, and dTTP are added to the synthesis mixture, either separately or together with the primers, in adequate amounts and the resulting solution is heated to about 90°-100° C. from about 1 to 10 minutes, preferably from 1 to 4 minutes. After this heating period, the solution is allowed to cool to approximately room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, E. coli DNA polymerase I, Klenow fragment of E. coli DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation such as Taq DNA polymerase, and the like). Suitable enzymes will facilitate combination of the nucleotides in the proper manner to form the primer extension products which are complementary to each locus nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

Preferably, the method of amplifying is by PCR, as described herein and as is commonly used by those of ordinary skill in the art. However, alternative methods of amplification have been described and can also be employed. PCR techniques and many variations of PCR are known. Basic PCR techniques are described by Saiki et al. (1988 Science 239:487-491) and by U.S. Pat. Nos. 4,683,195, 4,683,202 and 4,800,159, which are incorporated herein by reference.

The conditions generally required for PCR include temperature, salt, cation, pH and related conditions needed for efficient copying of the master-cut fragment. PCR conditions include repeated cycles of heat denaturation (i.e. heating to at least about 95° C.) and incubation at a temperature permitting primer: adaptor hybridization and copying of the master-cut DNA fragment by the amplification enzyme. Heat stable amplification enzymes like the pwo, Thermus aquaticus or Thermococcus litoralis DNA polymerases are commercially available which eliminate the need to add enzyme after each denaturation cycle. The salt, cation, pH and related factors needed for enzymatic amplification activity are available from commercial manufacturers of amplification enzymes.

As provided herein an amplification enzyme is any enzyme which can be used for in vitro nucleic acid amplification, e.g. by the above-described procedures. Such amplification enzymes include pwo, Escherichia coli DNA polymerase I, Klenow fragment of E. coli DNA polymerase I, T4 DNA polymerase, T7 DNA polymerase, Thermus aquaticus (Taq) DNA polymerase, Thermococcus litoralis DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, E. coli DNA ligase or Q.beta replicase. Preferred amplification enzymes are the pwo and Taq polymerases. The pwo enzyme is especially preferred because of its fidelity in replicating DNA.

Once amplified, the nucleic acid can be attached to a solid support, such as a membrane, and can be hybridized with any probe of interest, to detect any nucleic acid sequence. Several membranes are known to one of skill in the art for the adhesion of nucleic acid sequences. Specific non-limiting examples of these membranes include nitrocellulose (NITROPURE) or other membranes used in for detection of gene expression such as polyvinylchloride, diazotized paper and other commercially available membranes such as GENESCREEN, ZETAPROBE (Biorad), and NYTRAN Methods for attaching nucleic acids to these membranes are well known to one of skill in the art. Alternatively, screening can be done in a liquid phase.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/ 0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically. In general, conditions of high stringency are used for the hybridization of the probe of interest The probe of interest can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the probe, or will be able to ascertain such, using routine experimentation.

In one embodiment, representational difference analysis (RDA, see Lisitsyn et al., Science 259:946-951, 1993, herein incorporated by reference) can be performed on CpG-containing nucleic acid following MCA. MCA utilizes kinetic and subtractive enrichment to purify restriction endonuclease fragments present in one population of nucleic acid fragments but not in another. Thus, RDA enables the identification of small differences between the sequences of two nucleic acid populations. RDA uses nucleic acid from one population as a "tester" and nucleic acid from a second population as a "driver" in order to clone probes for single copy sequences present in (or absent from) one of the two populations. In one embodiment, nucleic acid from a "normal" individual or sample, not having a disorder such as a cell-proliferative disorder is used as a "driver," and nucleic acid from an "affected" individual or sample, having the disorder such as a cell proliferative disorder is used as a "tester." In one embodiment, the nucleic acid used as a 'tester" is isolated from an individual having a cell proliferative disorder such as low grade astrocytoma, anaplastic astrocytoma, glioblastoma, medulloblastoma, gastric cancer, colorectal cancer, colorectal adenoma, acute myelogenous leukemia, leukemia, lung cancer, renal cancer, breast cancer, prostate cancer, endometrial cancer and neuroblastoma. The nucleic acid used as a "driver" is thus normal astrocytes, normal glial cells, normal brain cells, normal gastric cells, normal colorectal cells, normal leukocytes, normal lung cells, normal kidney cells, normal breast cells, normal prostate cells, normal uterine cells, and normal neurons, respectively, hi an additional embodiment, the nucleic acid used as a "driver" is isolated from an individual having a cell proliferative disorder such as low grade astrocytoma, anaplastic astrocytoma, glioblastoma, medulloblastoma, gastric cancer, colorectal cancer, colorectal adenoma, acute myelogenous leukemia, leukemia, lung cancer, renal cancer, breast cancer, prostate cancer, endometrial cancer and neuroblastoma. The nucleic acid used as a "tester" is thus normal astrocytes, normal glial cells, normal brain cells, normal gastric cells, normal colorectal cells, normal leukocytes, normal lung cells, normal kidney cells, normal breast cells, normal prostate cells, normal uterine cells, and normal neurons, respectively. One of skill in the art will readily be able to identify the "tester" nucleic acid useful with to identify methylated nucleic acid sequences in given "driver" population.

The materials for use in the assay of the invention are ideally suited for the preparation of a kit Therefore, in accordance with another embodiment of the present invention, there is provided a kit useful for the detection of a cellular proliferative disorder in a subject having or at risk for the cellular proliferative disorder. Invention kits include a carrier means compartmentalized to receive a sample in close confinement therein, one or more containers comprising a first container containing a reagent which modifies unmethylated cytosine and a second container containing primers for amplification of a CpG-containing nucleic acid, wherein the primers distinguish between modified methylated and nonmethylated nucleic acid, and optionally, a third container containing a methylation sensitive restriction endonuclease. Primers contemplated for use in accordance with the invention include those that would amplify sequences or fragments thereof as set form in SEQ ID NOS: 1-64.

In another aspect, the kit is ideally suited for high throughput automated analysis. Thus, the kit further comprises a plurality of nucleotides arranged in an array on a solid support such as a microchip, a glass slide, or a bead, which can be contacted serially or in parallel with test samples as prepared above.

Carrier means are suited for containing one or more container means such as vials, tubes, and the like, each of the container means comprising one of the separate elements to be used in the method. In view of the description provided herein of invention methods, those of skill in the art can readily determine the apportionment of the necessary reagents among the container means. For example, one of the container means can comprise a container containing an oligonucleotide for ligation to nucleic acid cleaved by a methylation sensitive restriction endonuclease. One or more container means can also be included comprising a primer complementary to the oligonucleotide. In addition, one or more container means can also be included which comprise a methylation sensitive restriction endonuclease. One or more container means can also be included containing an isoschizomer of the methylation sensitive restriction enzyme.

It should be noted that as used herein and in the appended claims, the singular forms "a," "and," and "the" include plural referents unless the context clearly dictates otherwise. Thus, for example, reference to "a cell" includes a plurality of such cells and reference to "the restriction enzyme" includes reference to one or more restriction enzymes and equivalents thereof known to those skilled in the art, and so form.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference in full for the purpose of describing and disclosing the methodologies which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are intended to illustrate but not to limit the invention in any manner, shape, or form, either explicitly or implicitly. While they are typical of those mat might he used, other procedures, methodologies, or techniques known to those skilled in the art may alternatively be used.

Example 1

Materials and Methods

A. Collection and Preparation of Pancreatic Cell lines

Twenty-two human pancreatic cancer cell lines and immortal cell line derived from normal human pancreatic ductal epithelium (HPDE; provided by Dr. Ming-Sound Tsao, University of Toronto, Toronto, Ontario, Canada) were used in this study. Primary pancreatic carcinoma tissues were obtained from surgical specimens resected at The Johns Hopkins Medical Institutions and microdissected to enrich neoplastic cellulairity as described in Ueki, Cancer Res., 60:1835-1839,2000; UeM, Cancer Res., 61:8540-8546, 2001). Normal pancreatic duct epithelial cells were selectively microdissected from resected pancreata from 10 patients (mean age, 64.3 years; range, 36-83 years) with various pancreatic disorders using a laser capture microdissection system. Pancreatic juice samples were collected from 37 patients (mean age, 62.9 years; range 31-81 years) undergoing pancreaticduodenectormy for pancreatic ductal adenocarcinoma (24 patients), chronic pancreatitis (8 patients), islet cell tumor (4 patients), and serous cystadenoma (1 patient). Pancreatic juice was retrieved by direct aspiration from the transected pancreatic duct at the time of surgical resection.

B. Treatment with 5Aza-dC and/or TSA

Four pancreatic cancer cell lines (AsPC1, Hs766T, MiaPaCa2, and Panc1) were treated with 5Aza-dC (sigma, St Louis, Mo.) and TSA (Sigma), wither alone or in combination. Cells were exposed continuously to 5Aza-dC (1 µM) for 4 days or to TSA (1 µM) for 24 h. It was observed that treatment of the cell lines with 5Aza-dC (1 µM) for 4 days resulted in marked induction of several genes silenced by aberrant methylation without evidence for cell death. Mocktreated cells were cultured with the equivalent volume of PBS alone. For combined treatment, these cells were cultured in the presence of 5Aza-dC (1 µM) for 3 days and then treated for another 24 h with TSA (0.5 µM).

C. Oligonucleotide Array Hybridization

Total RNA was isolated from cultured cells using TRIZOL reagent (invitrogen, Carlsbad, Calif.) and purified using RNeasy Mini Kit (Qiagen, Valencia, Calif.). First- and second-stranded cDNA was synthesized from 10 µg of total RNA using 17-dT) primer (Genset Corp., La Jolla, Calif.) and Superscript Choice system (Invitrogen). Labeled cRNA was synthesized from the purified cDNA by in vitro transcription reaction using the BioArray High Yield RNA Transcript Labeling Kit (Enzo Diagnostics, Inc., Farmingdale, N.Y.) at 37° C. for 6 h. The cRNA was fragmented at 94° C. for 35 min. in a fragmentation buffer [40 mM Tris-acetate @ pH 8.1, 100 mM potassium acestate, and 30 mM magnesium acetate]. The fragmented cRNA was then hybridized to the Human Genome U133A chips (Affymetrix, Santa Clara, Calif.) with 18462 unique gene/EST transcripts at 45° C. for 16 h. The washing and staining procedure was performed in the Affymetrix Fluidics Station according to the manufacturer's instructions. The probes were then scanned using a laser scanner, and signal intensity for each transcript (background-subtracted and adjusted for noise) was calculated using Microarray Suite Software 5.0 (Affymetrix).

D. Reverse Transcription-PCR (RT-PCR)

Four µg of total RNA were reverse transcribed using Superscript II (Invitrogen). PCR reaction was performed under the following conditions: (a) 95° C. for 5 min.; (b) 30-35 cycles of 95° C. for 20 s, 60° C. for 20 s, and 72° C. for 20 s; and (c) a final extension of 4 min. at 72° C. Primer sequences were

```
                               SEQ ID NO: 65
5'-CTCTGTTTAGCACTGATAATG-3' (forward),
and SEQ ID NO: 66 for CDH3;
5'-TTTATTAGACTTGAGCTGATTC-3' (reverse), SEQ ID NO: 67
5'-CATCGAGCTGCTCATCAAC-3' (forward),
and SEQ ID NO: 68 for CNPTX2;
5'-CTGCTCTTGTCCAAGGATC-3' (reverse), SEQ ID NO: 69
5'-CTGGCCCGAGATGCTTAAG-3' (forward),
and SEQ ID NO: 70 for SARP2;
5,-TATTTTCATCCTCAGTGCAAAC-3, (reverse), SEQ ID NO: 71
5'-CnCATGAAGCAGACCATTG-3' (forward),
and
```

-continued
```
                       SEQ ID NO: 72 for UCHL1;
5'-ATCATGGGCTGCCTGTATG-3' (reverse),
and SEQ ID NO: 73
5'-CGGGAGATCAAGCAGAATC-3' (forward),
and SEQ ID NO: 74 for WNT7α.
5'-AACGGCCTCGTTGTACTTG-3' (reverse),
```

Glyceraldehyde-2-phosphate dehydrogenase (GAPDH) was also amplified as a control to ensure the cDNA integrity.

E. Bisulfite Treatment and Methylation-Specific FOR (MSP)

Methylation status of the 5' CpG island of each gene was determined by MSP as described by Herman, *Proc. Natl. Acad Sci. USA,* 93:9821-9826, 1996. DNA samples were treated with sodium bisulfite (Sigma) for 16 h at 50° C. After purification with the Wizard DNA clean-up system (Promega, Madison, Wis.), 1 µg of bisulfite-treated DNA was amplified using primers specific for either methylated or tramethylated DNA. Primers were designed to detect the sequence differences between methylated and unmethylated DNA as a result of bisulfite modification, and each primer pair contained at least four CpG sites to provide optimal specificity. Primer sequences for 16 genes analyzed in this study are disclosed in Table 4. PCR conditions were as follows: (a) 95° C. for 5 mm.; (b) 40 cycles of 95° C. for 20 s, 60° C.-62° C. for 20 s, and 72° C. for 30 s; and (c) a final extension of 4 min, at 72° C. 5 µl of each PCR product were loaded onto 3% agarose gels and visualized by ethidium bromide staining.

F. Statistics

Fold change analysis of signal intensities obtained from oligonucleotide microarrays between the two treatment groups was performed using Data Mining software (Afrymetrix). The frequency of aberrant methylation in pancreatic juice samples between patients with pancreatic cancer and those with other pancreatic diseases was compared using Fisher's exact probability test.

Example 2

Identification of Genes Induced by 5Aza-dC in Pancreatic Cancer Cell Lines

The global changes in gene expression proxies induced by 5Aza-dC in four pancreatic cancer cell lines (AsPCl, Hs766T, MiaPaCa2, and Panel) were determined using the Afrymetrix U133 oligonucleotide microarrays with 18462 probes sets (transcripts) covering over 13000 full-length sequences of known genes. Compared with mock-treated counterparts, 5Aza-dC treatment resulted in a substantial increase (>5-fold) in signal intensities of 225 transcripts (1.2% of the 18462 trancripts analyzed) in AsPCl, 167 transcripts (0.9%) in Hs766T, 251 transcripts (1.4%) in MiaPaCa2, and 116 transcripts (0.6%) in Panc1. The gene expression changes in nonneoplastic ductal cell line HPDE treated with 5Aza-dC identified 101 transcripts (0.5%) whose expression was induced after drug treatment. Forty-one transcripts that were also reactivated in the nonneoplastic HPDE cell line were excluded from the 631 candidates to identify genes that were aberrantly methylated specifically in pancreatic cancer but not in normal pancreatic ductal epithelium. This left 590 transcripts (487 known genes and 103 expressed sequence tags) specifically up-regulated by 5Aza-dC treatment in pancreatic cancers. Of these 487 known genes, 10 were represented by two or more probes sets, resulting in 475 genes identified as markedly up-regulated by 5Aza-dC treatment in one or more pancreatic cancer cell lines but not in the non-neoplastic HPDE cells. Table 1 lists the data for the 50 most interesting genes identified.

Of note, this large panel of genes includes several cancer testis antigens (G antigens, and so forth), IFN-related genes (TFN-stimulated gene, and so forth), and imprinted genes (insulin-like growth factor II), which is consistent with previous reports of genes inducible by 5Aza-dC. Although several genes have been reported to be induced by 5Aza-dC treatment independent of the methylation status of their 5' CpG islands, many of the genes identified here may represent potential targets for aberrant methylation in pancreatic cancer. In fact, our approach identified several genes previously reported to be aberrantly methylated in pancreatic and other cancers, such as CACNA1G, CDKN1A/p21, p57KIP2, stratifin/14-3-3σ, and TIMP-3.

Example 3

Identification of Genes Induced by TSA in Pancreatic Cancer Cell Lines

The global changes in gene expression profiles induced by the histone deacetylase inhibitor TSA in the same four pancreatic cancer cell lines were analyzed. Treatment with TSA resulted in a marked induction of 424 transcripts (2.3% of the 18642 transcripts analyzed) in AsPC1, 349 transcripts (1.9%) in Hs766T, 207 transcripts (1.1%) in MiaPaCa2, and 459 transcripts (2.5%) in Panel. Overall, 1196 transcripts (6.5%) including 965 genes and 231 expressed sequence tags were induced 5-fold or greater by TSA in one or more of the four pancreatic cancer cell lines. These include a large panel of novel targets for silencing by histone deacetylation including several known tumor suppressor genes or cell cycle-regulatory genes (ING1, p57KIP2, CHES1, CHFR, GADD45B, and others). Many of the genes induced by TSA treatment were also induced by 5Aza-dC treatment alone, suggesting a role for both DNA methylation and histone deacetylation in the transcriptional regulation of these genes. Interestingly, treatment of Hs766T with TSA but not with 5Aza-dC resulted in a significant increase in expression of many cancer testis antigens (e.g., G antigens), whereas these genes were inducible by treatment with 5Aza-dC but not with TSA in the other three cell lines.

Example 4

Identification of Genes Induced by Treatment of Pancreatic Cancer Cell Lines with Both Agents The gene expression profiles in four pancreatic cancer cell lines after combined treatments with 5Aza-dC and TSA was determined. Treatment with both agents resulted in induction of 422 (2.3%) of the 18462 transcripts in AsPC1, 304 transcripts (1.6%) in Hs766T, 243 transcripts (1.3%) in MiaPaCa2, and 196 transcripts (1.1%) in Panc1. Overall, 857 transcripts (1.6%) corresponding to 707 genes and 150 expressed sequence tags were induced in at least one of the four pancreatic cancer cell lines. The 707 genes induced by the combined treatment include several genes known to be aberrantly methylated in cancers (e.g., p16 and MLH1), supporting a previous notion that some of the genes with densely methylated CpG islands are reexpressed by a combined treatment with 5Aza-dC and TSA. Although treatment of all of the four pancreatic cancer cell lines with 5Aza-dC alone or TSA alone did not result in apparent changes in their phenotypes during the treatment period, combined treatment of certain pancreatic cancer cell lines with 5Aza-dC and TSA induced cell death in a small fraction of cells.

Example 5

Expression and Methylation Analysis of Selected Genes in Pancreatic Cancer Cell Lines Novel targets for aberrant methylation in pancreatic cancer were identified using 16 candidate genes that have been reported to be cancer associated or considered functionally important from the list of 457 genes identified as markedly (>5-fold) up-regulated by 5Aza-dC treatment in one or more of pancreatic cancer cell lines but not in the nonneoplastic HPDE cells. The genes are listed in Table 4. A literature search using PubMed revealed that 14 of the 16 genes have not been implicated for aberrant methylation in any tumor type, whereas SARP2 (also termed (SFRP1) and TJP2 (alos termed ZO-2) have been recently reported to be frequently methylated in colorectal and pancreatic cancers, respectfully. All of the 16 genes were identified as having CpC-rick sequences fulfilling the criteria of CpG island [GC content>50%, CpG:GpC ratio>0.6, and minimum length (200 bp)] in their 5' regions.

RT-PCR was performed on 5 (CDH3, NPTX2, SARP2, UCHL1, and WNT7A) of these 16 genes in two pancreatic cancer cell lines (AsPC1 and MiaPaCa2) to compare the results with the corresponding microarray d£ta and found concordant results (FIG. 1A).

Figure 1B:
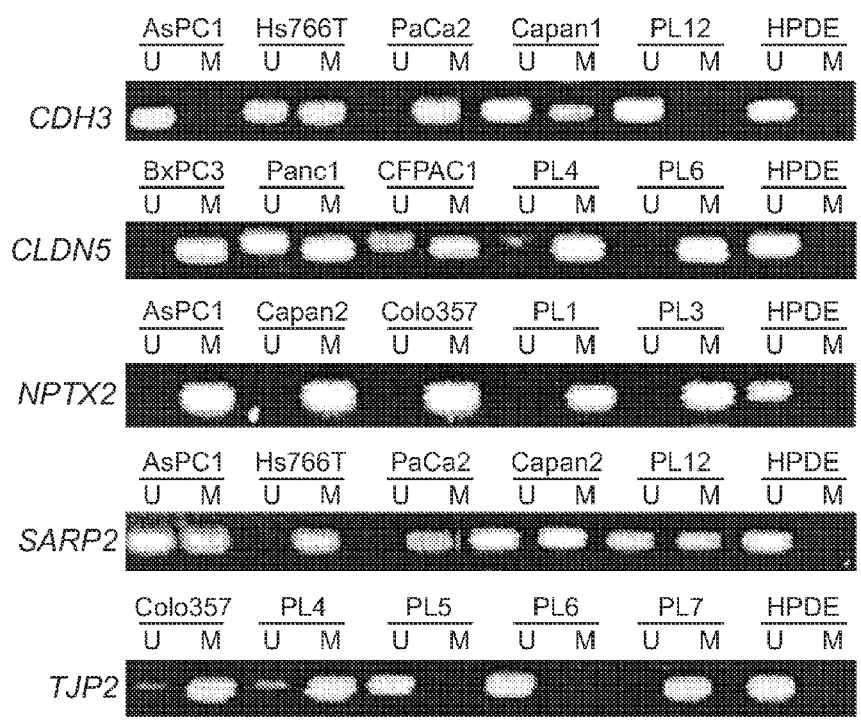
Figure 2:
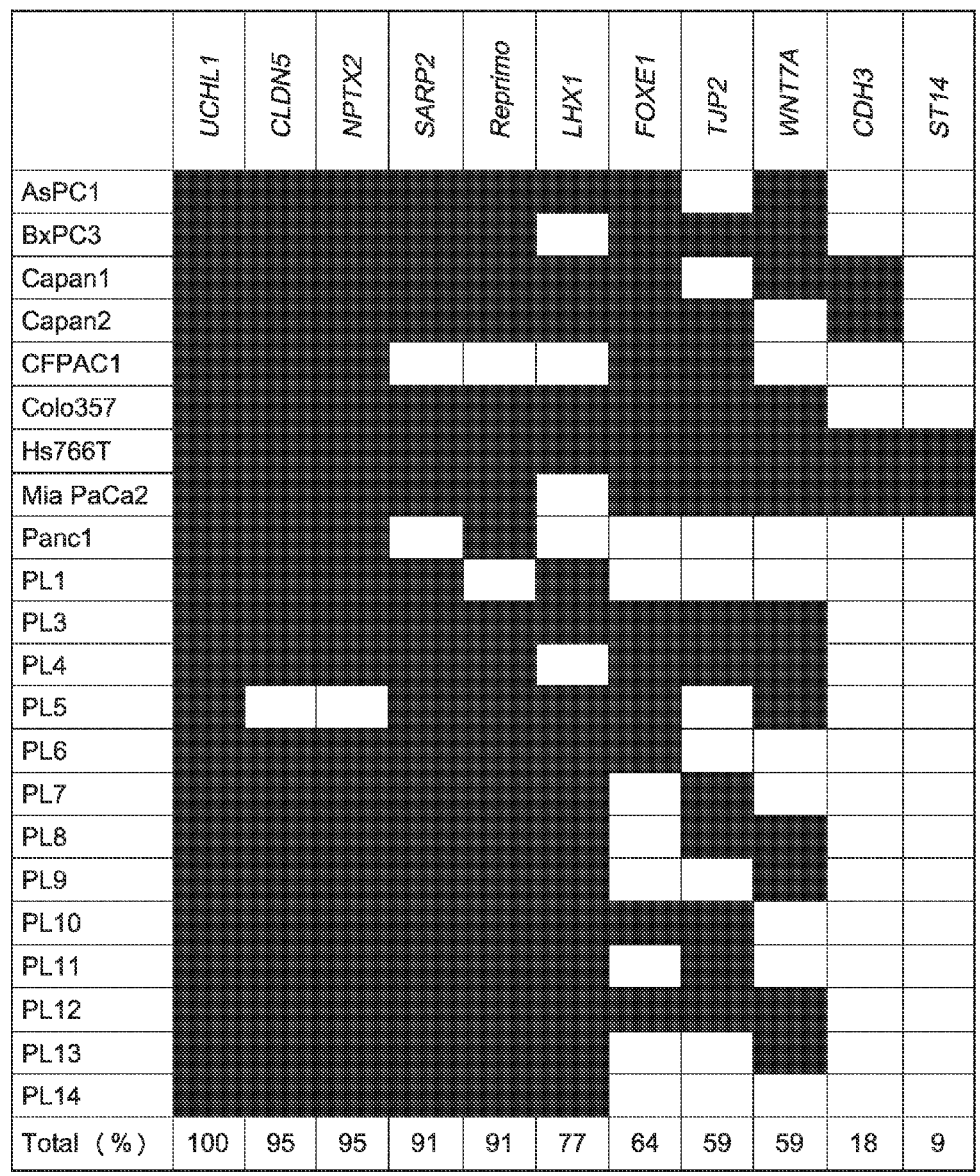
FIG. 2 is a graphical diagram summarizing the methylation profiles of 11 genes in a panel of 22 pancreatic cancer cell lines determined by MSP. Filled boxes are methylated alleles, open boxes are unmethylated alleles.

The methylation status of the 16 genes was then determined in the nonneoplastic HPDE cells. By MSP, five of these genes (DR3, LDOC1, NEFH, PIG11, and SMARCA1) showed partial methylation in HPDE and were excluded from further analysis. The remaining 11 genes were completely unmethylated in HPDE, and the methylation status of these 11 genes was determined in a panel of 22 pancreatic cancer cell lines. Hypermethylation of all 11 of these genes was found in varying frequencies as depicted in FIG. 1B. The most frequently methylated was UCHL1 (methylated in 100%), followed by CLDN5 (95%), SARP2 (91%), reprimo (91%), LHX1 (77%), FOXE1 (64%), TJP2 (59%), WNT7A (59%), CDH3(18%), and ST14 (9%). The number of aberrantly methylated genes varied among individual cell lines, with an average number of loci of 7.6 (range 4-11) per cell line (FIG. 2). There was no significant correlation between the number of methylated loci and the genetic profile of cell lines with regard to the presence or absence of mutations in the K-ras, p53, and/or SMADA4 genes.

Example 6

Figure 3:
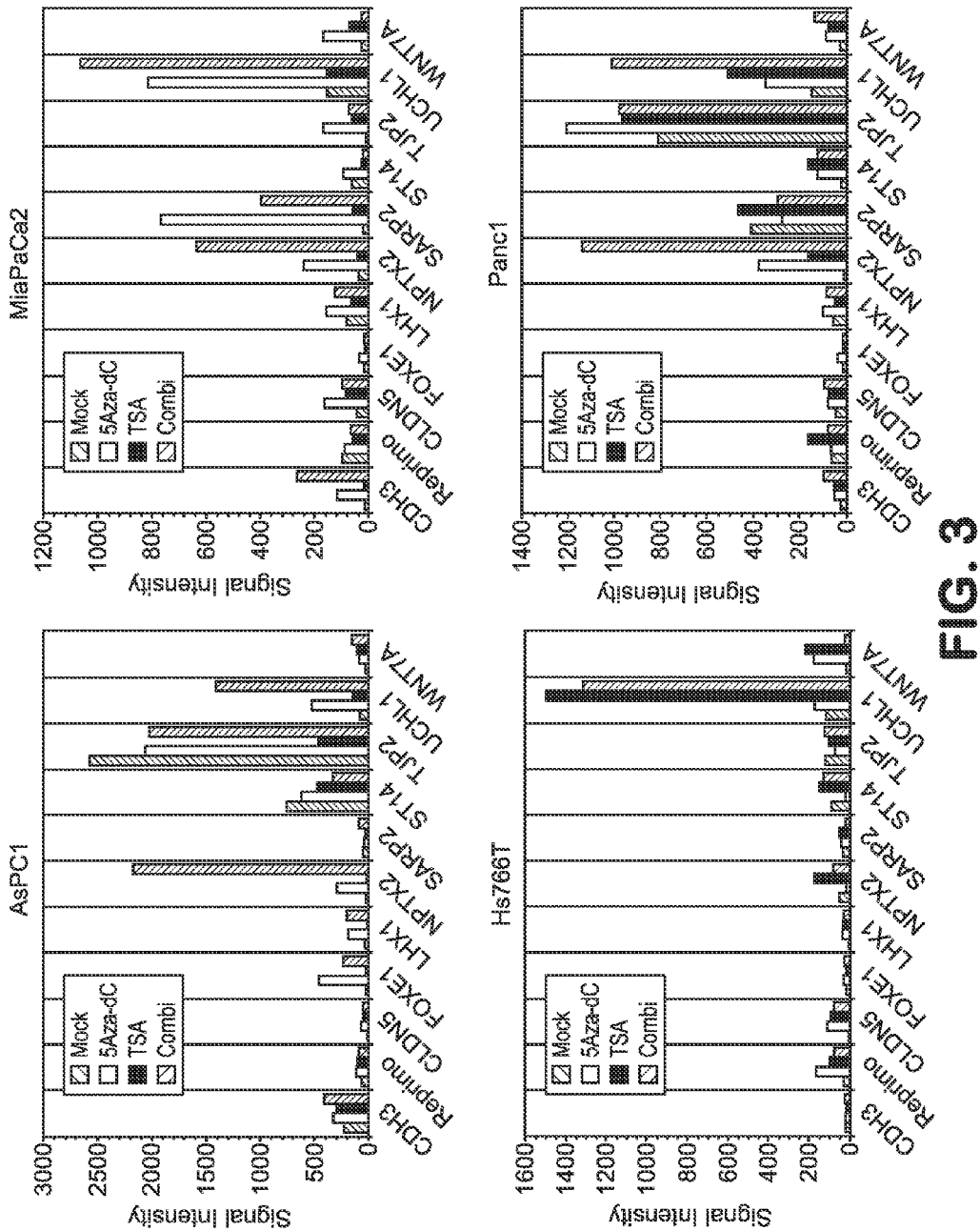
FIG. 3 shows graphical expression patterns of 11 genes aberrantly methylated in pancreatic cancer after treatment with 5Aza-dC, TSA, or a combination of both in four pancreatic cancer cell lines. Cells were treated with 5Aza-dC alone, TSA alone, or a combination of both, and subjected to oligonucleotide microarray hybridization.

Pattern of Changes in Expression of Genes Aberrantly Methylated in Pancreatic Cancer Cells The relationship between methylation status of the genes identified as aberrantly methylated in pancreatic cancer with the change in expression levels after treatment with 5Aza-dC and/or TSA was then analyzed. The microarray data to compare the expression of the 11 genes among all the treatment groups in each of the four pancreatic cancer cell lines indicated that the most common pattern was weak or moderate induction after 5Aza-dC treatment, and strong (synergistic) induction after combined treatment (FIG. 3). However, some of the genes were also induced by TSA treatment alone (e.g., UCHL1 in Hs766T and Panc1). Furthermore, reexpression of genes completely methylated in an individual cell line was not observed after 5Aza-dC or combined treatment (e.g., reprimo in MiaPaCa2 and SARP2 in Hs766T). It maybe due to the primers used not covering the critical region or transcriptional regulation, ft is also possible that other mechanisms besides DNA methylation and histone deacetylation could be involved in the silencing of these genes.

Example 7

Methylation Analysis of Multiple Genes in Primary Pancreatic Cancers

To test whether the aberrant methylation of the genes identified in pancreatic cancer cell lines also occurred in primary pancreatic cancers, the methylation status of the 11 genes in 20 primary pancreatic cancers and 10 normal pancreatic ductal epithelia was analyzed. Aberrant methylation was also detected in 100% of primary pancreatic cancers for UCHL1, 100% of primary pancreatic cancers for NP1X2, 100% of primary pancreatic cancers for SARP2, 90% of primary pancreatic cancers for CLDN5, 85% of primary pancreatic cancers for WNT7A, 80% of primary pancreatic cancers for reprimo, 75% of primary pancreatic cancers for LHX1, 75% of primary pancreatic cancers for FOXE1, 70% of primary pancreatic cancers for TJP2, 20% of primary pancreatic cancers for CDH3, and 10% of primary pancrfeatic cancers for ST14. By contrast, 8 of 11 genes were completely unmethylated in all 10 of the samples from normal pancreatic ductal epithelia. Three genes (UCHL1, WNT7A, and FOXE1) showed a weak amplification of methylated alleles in 1-3 of the 10 normal pancreatic ductal epithelia. These results confirm the abnormal methylation patterns of these 11 genes in primary pancreatic carcinomas as well as in pancreatic cancer cell lines.

Example 8

Figure 4:
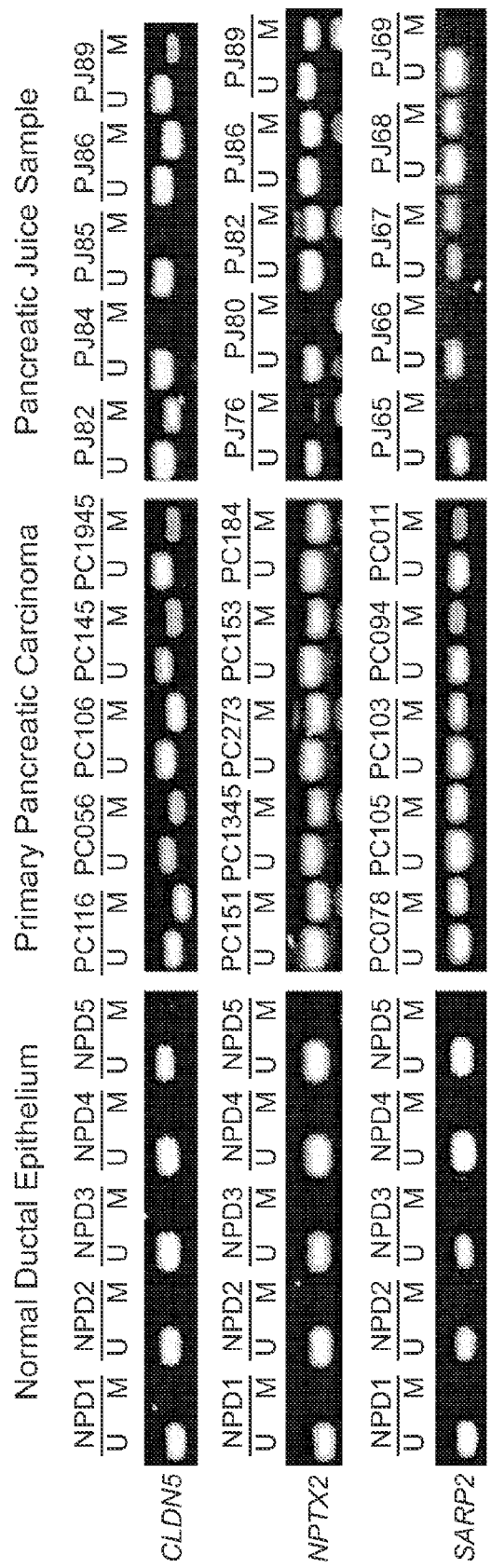
FIG. 4 shows MSP analysis of three genes (CLDN5, NPTX2, and SARP2) in a series of normal pancreatic ductal epithelia, primary pancreatic carcinomas, and pancreatic juice samples. The PCR products in Lanes U and M indicated the presence of unmethylated and methylated templates, respectively.

Methylation Analysis of Selected Genes in a Larger Panel of Primary Pancreatic Cancers and in Pancreatic Juice Samples To test the diagnostic potential of genes identified as methylated in pancreatic cancer, three genes (NPTX2, SARP2, and CLDN5) were selected. These three genes were found to be frequently methylated in pancreatic cancer and not methylated in any of the normal ductal epithelia studied. To confirm the high prevalence of aberrant methylation at these loci, the methylation status of the genes in an expanded series of 43 surgically resected, primary pancreatic cancers, was analyzed. Aberrant methylation of NPTX2, SARP2, and CLDN5 was detected in 42 (98%), 41 (95%), and 35 (81%) of these 43 primary pancreatic cancers (FIG. 4), and hypermethylation of at least one of these loci was found in 100% of the primary tumors tested.

Pancreatic juice samples collected from patients with pancreatic cancer as described above, was then subject to analysis to determine whether aberrant hypermethylation of NPTX2, SARP2, and CLDN5 could be detected. Using MSP, a total of 37 pancreatic juice samples including 24 samples from patients with pancreatic cancer and 13 samples from patients with benign pancreatic disorders were analyzed for the methylation patterns of the three genes. Aberrant methylation of NPTX2 in 67%, of SARP2 in 46%, and of CLDN5 in 42% of the 24 juice samples from patients with pancreatic cancer. Overall, 75% (18 of 24) of juice samples from pancreatic cancer patients exhibited aberrant methylation of at least one gene, whereas none of the 13 juice samples from patients with benign pancreatic diseases harbored hypermethylation of any of these genes (P<0.0001). Importantly, aberrantly methylated DNA was detected in the five juice samples from patients with small pancreatic cancers (tumor <2 cm in diameter).

Example 9

Summary

To identify potential targets for aberrant methylation in pancreatic cancer, gene expression profiles of four pancreatic cancer cell lines were analyzed after exposure to 5Aza-dC and/or TSA. A substantial number of genes were identified as having expression that was markedly induced by 5Aza-dC and TSA, either alone or in combination. Using MSP, the abnormal methylation patterns of 11 selected genes were confirmed in pancreatic cancer cells and in a series of resected primary pancreatic carcinomas. Most these genes have not been implicated as sites of aberrant methylation in any tumor type. These results demonstrate that gene expression profiling can be used to identify novel target genes that display aberrant methylation in pancreatic cancer. It was also demonstrated that these aberrantly methylated genes can be detected in a significant proportion of pancreatic juice samples from patients with pancreatic cancer but not in juice samples from patients with benign pancreatic disorders. The results support that aberrant hypermethylation of multiple genes is a common event in pancreatic cancer and suggest that these genes can be sensitive and specific markers for the early detection of pancreatic cancer.

Recently, Suzuki et al. (*Nat. Genet.*, 31:141-149, 2002.) have described a cDNA microarray-based approach to screen for genes epigenetically silenced in colorectal cancer. They studied gene expression profiles in colorectal cancer cell line (RKO) treated with 5Aza-dC and/or TSA and successfully identified a number of genes harboring CpG island hypermethylation in colorectal cancer cell lines and in primary tumors; however, some of these genes were also methylated in normal colonic tissues. Although slight methylation was occasionally noted in only a small number of samples from normal pancreatic ductal epithelia, most of the genes identified as aberrantly methylated in pancreatic cancer were completely unmethylated in a panel of normal pancreatic ductal epithelia.

An advantage of using high-throughput oligonucleotide microarray data from multiple cell lines is the ability to identify a substantial number of candidates genes targeted for aberrant methylation in human cancers. Such data also provides the ability to conservatively estimate the number of genes directly affected by aberrant methylation in pancreatic cancers. Treatment of pancreatic cancer cell lines with 5Aza-dC induced an average of ~200 transcripts (range 116-251 transcripts) per cell line. Sixteen genes with CpG islands were selected from the list of genes induces by 5Aza-dC in pancreatic cancer cell lines but not in nonneoplastic HPDE cells, and it was confirmed that ~70% (11 of 16) of these genes were aberrantly methylated in pancreatic cancer. Therefore, an average of 140 genes (70% of 200 genes) may be aberrantly methylated in a pancreatic cancer cell line, of which 60 would be expected to be CpG islands [one previous study has estimated that 60% of genes induced by 5Aza-dC do not have CpG islands within their 5' regions]. Sixty aberrantly methylated CpG islands in a pancreatic cancer is considered to be a minimum estimate for several reasons: analysis did not include a large fraction of ESTs on the Affymetrix U133B chip; expression of many genes that harbor aberrantly methylated CpG islands may be unaffected by 5 Aza-dC treatment;

and because of the use of a stringent 5-fold induction of expression as a cutoff for identifying genes induced by 5Aza-dC.

Previously, Costello et al. (*Nat Genet.*, 24:132-138, 2000.) studied a pair of cancers using RLGS and estimated that ~600 CpG islands were aberrantly methylated in a given cancer. Their estimate is higher than ours for a number of reasons. RLGS also identifies methylated CpG islands that are unrelated to genes (~22% of CpG islands in their study). Treatment with 5Aza-dC induced the expression of only one-third of the CpG islands they identified as hypermethylated in tumors. In addition, RLGS may also identify methylated CpG islands in tumors when corresponding normal tissue has a low level methylation. This study and results highlight the fact that in human cancers, a substantial number of genes are silenced by aberrant methylation. Similarly, the large number of genes induced by TSA is consistent with previous reports that have found between 2% and 10% of genes are induced in cancer cells by TSA treatment Variability was observed in the gene expression response of individual cell lines to 5Aza-dC and to TSA. Some cell lines harboring methylation of CpC islands at a specific locus had induction of gene expression after 5Aza-dC treatment, whereas others did not. The same observation was true for TSA treatment. Surprisingly, none of the genes analyzed in this study showed induction (>5-fold) after 5Aza-dC treatment in all of the four pancreatic cancer cell lines, even when a gene was methylated in each of these cell lines. This may partly reflect the use of a 5-fold cutoff as an indicator of a significant induction of expression. It is also likely that differences in CpG island methylation density and different levels of transcriptional cofactors between different cell lines contribute to differences in gene expression responses to 5Aza-dC and to TSA. Because a panel of genes induced by 5Aza-dC treatment in even one of the four pancreatic cancer cell lines tested usually led to identifying aberrant CpG methylation of these genes in other pancreatic cancer cell lines, it proved helpful to provide a list of all genes induced 5-fold or greater by 5Aza-dC treatment.

A number of genes without 5' CpG islands were identified that were up-regulated after 5 Aza-dC treatment. These findings imply that even genes with poor CpG promoters can be regulated by DNA methylation. In keeping with this notion, it was observed that relatively CpG-poor genes such as 14-3-3a are aberrantly methylated in cancer. Genes induced by 5 Aza-dC mat are known to be overexpressed in pancreatic and other cancers (for example, kallikrein 10) were also identified. Interestingly, kallikrein 10 has previously been shown to be methylated in certain cancers. This observation suggests that alterations in methylation patterns may be responsible for the overexpression, as well as the underexpression, of many affected genes in cancer.

One of the novel findings in this study is that TS A alone could induce the expression of 4 of the 11 genes whose CpG islands were identified as aberrantly methylated in pancreatic cancer. In addition, several genes previously characterized as having methylated CpG islands (such as p57KIP2 and CACNA1G) were also reexpressed after treatment with TSA alone. Previous studies have found that TSA alone is not sufficient to induce the expression of genes with densely methylated CpG islands, although it can facilitate induction of gene expression when combined with 5Aza-dC. Recently El-Osta et al. (*Mol. Cell. Biol.*, 22:1844-1857, 2002) have reported that methyl-CpG-binding protein 2 is involved in methylation-dependent silencing of the MDR1 gene and that treatment with 5-azacytidine but not TSA can release methyl-CpG-binding protein 2 from the heavily methylated promoter, thereby leading to a partial relief of the transcriptional repression. Although the mechanisms underlying the correlation between DNA methylation and histone deacetylation in the control of gene expression are still under investigation, our results provide evidence that treatment with TSA alone can, at least in some cases, relieve the silencing of methylated genes in cancer cells.

Changes in methylation patterns play a crucial role in cancer development and progression. A number of genes identified herein as aberrantly methylated in pancreatic cancer have known important properties involved in cell cycle regulation (reprimo), apoptosis (SARP2), cell adhesion (CDH#), and tight junction barrier (CLDN5 and TJP2). Aberrant methylation and associated silencing of these genes may be functionally important for pancreatic carcinogenesis. For example, reprimo, which displayed frequent hypermethylation in pancreatic cancer, is a downstream mediator of p53-induced $G_2$ cell cycle arrest. When overexpressed, reprimo induces cell cycle arrest at the $G_2$ phase, suggesting it has tumor suppressor function. Because functional abrogation of the p53 tumor suppressor gene and its downstream mediators, such as 14-3-3σ, is central to the development of human cancers, it is likely that aberrant methylation of reprimo could lead to defects in cell cycle control and contribute to pancreatic neoplastic progression.

It is also shown that SARP2 is a frequent target for aberrant methylation in pancreatic cancer. SARP2 is a member of SARP gene families that counteract the Wnt oncogenetic signaling pathway, and this gene is considered to be involved in the regulation of apoptosis. Breast cancer cells transfected with SARP2 show an increased sensitivity to different proapoptotic stimuli. Therefore, inactivation of SARP2 by aberrant methylation may provide a growth advantage to cancer cells through increasing the cellular resistance to apoptosis. Interestingly, SARP2 ahs recently been identified as frequently hypermethylated in colorectal and gastric cancer, thus suggesting general involvement of this gene in tumorigenesis of digestive organs.

Although a growing number of genes have been identified as aberrantly methylated in various cancers, to date few genes have been reported that are aberrantly methylated in a large majority of cancers. The approach taken herein identified five genes (UCHL1, NPTX2, SARP2, CLDN5, and reprimo), each of which was aberrantly methylated in >80% of a panel of pancreatic cancer cell lines. Furthermore, all of the genes found to be methylated in pancreatic cancer cell lines were also methylated in primary pancreatic carcinomas. This supports the observation made herein that aberrantly methylated genes identified in cancer cell lines are often present in the primary cancers from which they were derived. Genes that are aberrantly methylated at a high frequency in a given cancer are particularly suitable for early cancer detection strategies.

Several studies have addressed the diagnostic utility of epigenetic markers in detection of cancer. Methylation abnormalities have been detected in blood or sputum of patients with lung cancer, in serum of patients with head and neck cancer, in ductal lavage fluid of patients with breast cancer, and in urine from patients with prostate and bladder cancer. In particular, the inclusion of multiple genes in these analyses appears to provide a highly sensitive and specific marker for cancer diagnosis. Using three markers, it was possible to detect aberrantly methylated DNA in 75% of pancreatic juice samples from patients with pancreatic cancer.

Although the invention has been described with reference to the presently preferred embodiment, it should be understood that various modifications can be made without departing from the spirit of the invention. Accordingly, the invention is limited only by the following claims.

TABLE 1

| Fold-change after 5Aza-dC treatment | | | | | Induced by TSA | CpG | | |
|---|---|---|---|---|---|---|---|---|
| AsPC1 | Hs766T | MiaPaCa | Pane1 | HPDE | alone? | Island? | Genbank# | Gene name (symbol) |
| 6.15 | −0.44 | 2.27 | 0.91 | −0.4 | No | No | NM_001147 | angiopoietin 2 (ANGPT2) |
| 6.12 | −1.75 | 21.32 | −1.07 | 1.23 | Yes | No | NM_004052 | BCL2adenovirus E1B 19 kD-interactmg protein 3 (BNIP3) |
| 1.97 | 1.36 | 8.59 | −1.04 | −1.06 | No | No | NM_004335 | bone marrow stromal cell antigen 2 (BST2) |
| −1.07 | 5.21 | −1.3 | −1.01 | 2.23 | No | Yes | NM_000465 | BRCA1 associated RING domain 1 (BARD1) |
| 1-44 | 0.89 | 5.79 | 2.31 | −1.08 | No | Yes | NM_001793 | cadherin 3, type 1, P-cadherin (placental) (CDH3) |
| 1.66 | 6.65 | −1.09 | 1.03 | 1.06 | No | Yes | NM_019845 | candidate mediator of the p53-dependent G2 arrest (reprimo) |
| 22.34 | 1.21 | 1.67 | 1.88 | 2.45 | No | Yes | NM_003277 | claudin5 (CLDN5) |
| 1.12 | 5.75 | 4.23 | −1.91 | −1.03 | Yes | Yes | M76453 | colony stimulating factor 1 (CSF1) gene |
| 1.48 | 5.28 | 1.09 | 1.52 | 1.5 | No | Yes | NM_004702 | cyclin E2 (CCNE2) |
| 2.21 | 1.04 | 7.04 | 1.93 | 1.33 | No | Yes | NM_000389 | cyclin-dependent kinase inhibitor 1A (p21, Cip1) (CDKN1 A) |
| 0.6 | 5.42 | 2.28 | 3.77 | 1.07 | Yes | Yes | NM_000076 | cyclin-dependent kinase inhibitor 1C (p57, Kip2) (CDKN1C) |
| 1.47 | −1.46 | 2.12 | S.19 | 1.01 | No | Yes | U72763 | death receptor 3 (DR3) |
| 3.51 | 5.63 | 3.8 | 1.7 | −1.1 | No | Yes | NM_004473 | Forkhead box E1 (thyroid transcription factor 2) (FOXE1) |
| −0.54 | 0.48 | 6.7 | 0.46 | −0.55 | Yes | Yes | NM_001468 | G antigen 1 (GAGE1) |
| 7-55 | −2.57 | 15.22 | 9.78 | 1.33 | No | No | NM_001473 | G antigen 3 (GAGE3) |
| 15.66 | −1.1 | 47.6 | 35.44 | 3.33 | Yes | Yes | NM_001474 | G antigen 4 (GAGE4) |
| 15.59 | 1.09 | 24.03 | 35.5 | 2.41 | Yes | Yes | NM_001476 | G antigen 6 (GAGE6) |
| 14.08 | −1.12 | 54.35 | 36.1 | 3.36 | Yes | Yes | NM_021123 | G antigen 7 (GAGE7) |
| 1.44 | 5.53 | 3.97 | 2.17 | −0.94 | Yes | No | M11734 | granulocytemacrophage colony-stimulating factor |
| 25.8 | −1.61 | 2.56 | 1.26 | −1.23 | No | Yes | S79910 | HOXA1 |
| 0.55 | −0.41 | 0.81 | 9.41 | −0.34 | No | Yes | NM_000612 | insulin-like growth factor 2 (somatomedin A) (IGF2) |
| −1.12 | 1.02 | 21.28 | −0.84 | 0.89 | No | No | NM_002201 | interferon stimulated gene (20 kD) (ISG20) |
| 4.48 | −4.46 | 11.03 | 1.2 | 1.33 | Yes | No | NM_022873 | interferon, alpha-inducible protein |
| 7.51 | −2.59 | −1.77 | 1.37 | −1.81 | No | No | NM_000877 | interleukin 1 receptor, type I (IL1R1) |
| 1.27 | 5.27 | 1.4 | −4.18 | 2.14 | No | Yes | NM_020655 | junctophilin 3 (JPH3) |
| 1.03 | 1.16 | 136.95 | −1.05 | 3.75 | No | No | BC002710 | kallikrein 10 (KLK10) |
| 8.99 | −1.86 | −1.01 | 9.19 | −1.12 | No | Yes | NM_012317 | leucine zipper, down-regulated in cancer I (LDOC1) |
| 5.22 | 1.92 | 1.89 | 1.79 | 1.01 | No | Yes | NM_005568 | LIM homeobox protein 1 (LHX1) |
| 1.52 | 4.45 | 2.27 | 7.32 | 1.7 | Yes | Yes | NM_030801 | MAGE1 protein (MAGE1) |
| −1.44 | 6.83 | −1.01 | 3.61 | −125 | Yes | No | NM_002379 | matrilin 1, cartilage matrix protein (MATN1) |
| 2.94 | −1.24 | 6.73 | 4.59 | −1.08 | Yes | Yes | NM_021076 | neurofilament, heavy polypeptide (200 kD) (NEFH) |
| 13.97 | −2.6 | 6.4 | 18.94 | 2.42 | Yes | Yes | U26662 | neuronal pentraxin II (NPTX2) |
| −1.22 | 1.04 | 5.45 | 1.04 | −1.58 | No | Yes | NM_006034 | p53-induced protein (PIGII) |
| 8.94 | 1.36 | −1.12 | 4.45 | 2.57 | No | Yes | NM_000280 | paired box gene 6 (aniridia, keratitis) (PAX6) |
| −1.15 | −1.73 | 6.4 | 2.13 | 4.9 | No | No | NM_000930 | plasminogen activator, tissue (PLAT) |
| 1.37 | 1.12 | 7.5 | 1.08 | 1.2 | No | Yes | NM_016445 | pleckstrin 2 (mouse) homolog (PLEK2) |
| 1.33 | 6.38 | 3.48 | 4.84 | −1.04 | No | No | NM_024411 | prodynorphin (PDYN) |
| −1.89 | 1.35 | 38.33 | −1.47 | 1.11 | No | Yes | AF017987 | secreted apoptosis related protein 2 (SARP2) |
| −1.48 | −1.64 | 34.77 | 1.21 | −1.46 | Yes | Yes | BC000329 | stratifin (14-3-3 sigma) |
| 14.06 | 1.01 | 4.96 | 6.84 | 4.8 | Yes | Yes | NM_012447 | stromal antigen 3 (STAG5) |
| −1.21 | −4.72 | 1.48 | 5.1 | −1.05 | Yes | Yes | NM_021978 | suppression of tumorigenicity 14 (colon carcinoma, matriptase, epithin) (ST14) |
| 7.89 | −0.79 | −1.07 | 1.01 | 3.54 | No | Yes | NM_0003069 | SWISNF related, matrix associated, actin dependent regulator of chromatin, subfamily a, member 1 (SMARCA1) |
| −1.23 | 1.6 | 9.61 | 1.57 | 1.09 | Yes | Yes | BC001451 | testin |
| −1.24 | −1.56 | 8.61 | 1.49 | 1.41 | No | Yes | NM_004817 | tight junction protein 2 (*zona occludens* 2) (TJP2) |
| 11.89 | −3.67 | 1 | 1.1 | 1.32 | No | Yes | NM_000362 | tissue inhibitor of metalloproteinase 3 (TIMP3) |
| −1.17 | −4.9 | 31.63 | 1.18 | −1.2 | No | No | NM_000594 | tumor necrosis factor (TNF superfamily, member 2) (TNF) |
| 6.62 | 1.45 | 5.27 | 2.37 | 1.95 | Yes | Yes | NM_004181 | ubiquitin carboxyl-terminal esterase LI (ubiquitin thiolesterase) (UCHL1) |
| 1.83 | 0.5 | 1.61 | 5.26 | 0.39 | Yes | Yes | AF126966 | voltage-dependent calcium channel alpha IG subunit a isoform (CACNA1G) |

TABLE 1-continued

| Fold-change after 5Aza-dC treatment | | | | Induced by TSA alone? | CpG Island? | Genbank# | Gene name (symbol) |
|---|---|---|---|---|---|---|---|
| AsPC1 | Hs766T | MiaPaCa | Panel | HPDE | | | |
| 2.7 | 9.03 | 6.24 | 3.57 | −1.23 | Yes | Yes | D83175 | wingless-type MMTV integration site family, member 7A (WNT7A) |
| 28.59 | −0.5 | 12.99 | 24.78 | −0.43 | Yes | Yes | NM_020411 | XAGE-1 protein (XAGE-1) |

TABLE 2

| Fold-change after TSA treatment | | | | Induced by 5Aza-dC alone? | CpG Island? | Genbank# | Gene name (symbol) |
|---|---|---|---|---|---|---|---|
| AsPC1 | Hs766T | MiaPaCa | Panel | | | | |
| 8.73 | 1.73 | 2.14 | 2.74 | No | Yes | NM_001674 | activating transcription factor 3 (ATF3) |
| 7.6 | 1.86 | 5.02 | 3.22 | No | Yes | NM_001124 | adrenomedullin (ADM) |
| 18.35 | 2.02 | 3.97 | 4.2 | No | Yes | NM_001657 | amphiregulin (schwannoma-derived growth factor) (AREG) |
| −1.77 | 6.72 | 1.75 | −1.13 | No | No | NM_001146 | angiopoietin 1 (ANGPT1) |
| 1.65 | 2.35 | 10.05 | 5.02 | No | Yes | NM_001197 | BCL2-mteracting killer (apoptosis-inducmg) (BIK) |
| 1.11 | −1.11 | −1.29 | 6.85 | Yes | Yes | AB035305 | cadherin-8 (CDH8) |
| 1.73 | 1.06 | 5.18 | 5.41 | No | Yes | NM_004055 | calpain 5 (CAPN5) |
| −1.47 | 5.14 | 1.15 | 1.01 | No | Yes | AF040708 | candidate tumor suppressor gene 21 protein |
| 13.22 | 11.83 | 13.25 | 1.5 | No | Yes | AF044076 | candidate tumor suppressor p33ING1 (ING1) |
| −1.39 | 1.82 | 3.22 | 11.66 | No | Yes | NM_006569 | cell growth regulatory with EF-hand domain (CGR11) |
| 1.87 | −1.11 | −1.03 | 9.31 | No | Yes | NM_005197 | checkpoint suppressor 1 (CHES1) |
| −1.1 | 8 | 1.27 | −1.33 | No | Yes | NM_018223 | checkpoint with forkhead and ring finger domains (CHFR) |
| −4.26 | −1.81 | 1.13 | 8.69 | No | No | NM_014343 | claudin 15(CLDN15) |
| 17.38 | 43 | 4.28 | 7.69 | No | Yes | M92934 | connective tissue growth factor |
| 10.62 | 6.57 | 13.22 | 6.26 | Yes | Yes | NM_300076 | cyclin-dependent kinase inhihitor IC (p57, Kip2) (CDKN1C) |
| 4.56 | −1.26 | 5.91 | −2.06 | Yes | Yes | NM_004426 | early development regulator 1 (homolog of polyhomeotic 1) (EDR1) |
| 37.6 | 6.49 | 8.67 | 6.44 | No | Yes | NM_001965 | early growth response 4 (EGR4) |
| 1.91 | 7.43 | 1.7 | −1.37 | No | Yes | NM_001432 | epiregulin (EREG) |
| 0.66 | 14.57 | 0.53 | 0.63 | Yes | Yes | NM_001468 | G antigen 1 (GAGE1) |
| −2.5 | 432.64 | 1.31 | 1.4 | No | No | NM_001472 | G antigen 2 (GAGE2) |
| −5.88 | 184.93 | −2.68 | 1.07 | Yes | Yes | NM_001473 | G antigen 3 (GAGE3) |
| −1.67 | 234.36 | 1.32 | 2.29 | Yes | Yes | NM_001474 | G antigen 4 (GAGE4) |
| −1.16 | 237.45 | −2.17 | 1.62 | Yes | Yes | NM_001476 | G antigen 6 (GAGE6) |
| −4.88 | 331.97 | −1.76 | 3.56 | Yes | Yes | NM_001477 | G antigen 7B (GAGE7B) |
| 2.65 | 2.01 | 5.06 | −1.09 | No | Yes | AF087853 | growth arrest and DNA damage inducible protein beta (GADD45B) |
| 6.64 | 5.8 | 4.16 | 5.04 | No | Yes | BC002649 | H1 historic family, member 2 |
| 1.73 | 2.56 | 5.25 | 1.21 | No | Yes | NM_002133 | heme oxygenase (decycling) 1 (HMOX1) |
| 20.5 | 1.55 | 77.77 | 4.55 | Yes | Yes | NM_000558 | hemoglobin, alpha 1 (HBAI) |
| 2.18 | −1.12 | 14.09 | 3.03 | No | Yes | NM_006665 | heparanase (HPSE) |
| 10.26 | 5 | 2.27 | 21.22 | No | Yes | NM_002166 | inhibitor of DNA binding 2, dominant negative helix-loop-helix protein (ID2) |
| 44.67 | −1.42 | 1.36 | 3.01 | No | No | NM_000584 | interleukin 8 (1L8) |
| 7.63 | 1.54 | 2.91 | 2.13 | Yes | No | NM_019598 | kallikrein 12(KLK12) |
| 1.05 | 0.49 | 5.17 | 15.48 | Yes | Yes | NM_030801 | MAGE1 protein (MAGE1) |
| 9.05 | 1.63 | 1.01 | −2.63 | No | No | NM_002421 | matrix metalloproteinase 1 (interstitial collagenase) (MMP1) |
| 2.66 | 7.94 | 1.28 | −1.82 | No | Yes | NM_015845 | methyl-CpG binding domain protein 1 (MBD1) |
| 0.76 | 4.11 | 13.46 | 30.7 | Yes | Yes | NM_002507 | nerve growth factor receptor (TNFR superfamily, member 16) (NGFR) |
| 7.93 | 2.06 | −1.04 | 3.9 | No | Yes | NM_000435 | Notch (Drosophila) homolog 3 (NOTCH3) |
| 20.29 | 9.7 | 1.28 | −3.83 | Yes | Yes | NM_002616 | period (Drosophila) homolog 1 (PERI) |
| 1.08 | 5.74 | 2.74 | 3.69 | No | Yes | AF016535 | P-glycoprotein (mdr1) |
| 4.45 | 3.17 | 16.4 | 4.05 | Yes | Yes | AF003934 | prostate differentiation factor |
| 8 | 1.95 | 44.44 | 11.7 | No | Yes | NM_005025 | protease inhibitor 12 (neuroserpin) (SERPINU) |
| 413.37 | 1631 | 26.21 | 31.64 | No | Yes | NM_005794 | short-chain alcohol dehydrogenase family member (HEP27) |

TABLE 2-continued

| Fold-change after TSA treatment | | | | Induced by 5Aza-dC alone? | CpG Island? | Genbank# | Gene name (symbol) |
|---|---|---|---|---|---|---|---|
| AsPC1 | Hs766T | MiaPaCa | Pan1 | | | | |
| −0.78 | 15.92 | −1.34 | 6.45 | No | No | NM_013453 | sperm protein associated with the nucleus, X chromosome, family member A1 (SPANXA1) |
| 15.9 | −1.31 | 2.73 | 5.63 | Yes | No | NM_003155 | stanniocalcin 1 (STC1) |
| 1.74 | 38.74 | 1.5 | 2.73 | Yes | No | BC001003 | synovial sarcoma, X breakpoint 1 |
| 0.4 | 120.09 | −0.68 | 34.65 | No | Yes | L27624 | tissue factor pathway inhibitor-2 |
| 73.47 | 3.47 | 4.09 | 18.25 | Yes | Yes | NM_025217 | UL16-binding protein 2 (ULBP2) |
| 5.48 | −1.45 | 6.39 | 2.05 | No | Yes | U94592 | uncoupling protein homolog (UCPH) |
| 9.95 | 2.72 | 4.61 | 10.14 | Yes | Yes | AF126966 | voltage-dependent calcium channel alpha 1G subunit a isoform (CACNA1G) |
| 5.72 | 0.81 | 3.36 | 5.13 | Yes | Yes | NM_030761 | wingless-type MMTV integration site family, member 4 (WNT4) |

TABLE 3

| Fold-change after combined treatment | | | | Induced by 5Aza-dC alone? | Induced by TSA alone? | Genbank# | Gene name (symbol) |
|---|---|---|---|---|---|---|---|
| AsPC1 | Hs766T | MiaPaCa | Pan1 | | | | |
| 11.06 | 8.03 | 1.08 | 1.19 | No | Yes | AF193421 | activity-regulated cytoskeleton-associated protein (APC) |
| 2.96 | 8.04 | 4.8 | 2.13 | No | Yes | AB017332 | Auroralp11-related kinase 3 (aik3) |
| −1.5 | 13.56 | 2.23 | −1.31 | No | Yes | M27968 | basic fibroblast growth factor (FGF) |
| 9.73 | 8.23 | 10.27 | −1.08 | Yes | Yes | U15174 | BCL2adenovirusE1B 19 kD-interacting protein 3 (BNIP3) |
| 2.07 | 8.35 | 14.61 | 3.72 | No | Yes | NM_001197 | BCL2-interacting killer (apoptosis-inducing) (BIK) |
| 2.97 | 1.88 | 8.02 | −1.28 | Yes | No | NM_004335 | bone marrow stromal cell antigen 2 (BST2) |
| 5.59 | −1.22 | 1.28 | 1.13 | No | No | NM_004347 | caspase 5, apoptosis-related cysteine protease (CASP5) |
| −2.26 | 5.18 | 5.02 | 1.47 | No | No | BC005406 | Cdc42 effector protein 2 |
| 2.45 | 5.04 | 1.44 | 158 | No | No | NM_001789 | cell division cycle 25A (CDC25A) |
| 1.89 | 8.56 | 4.04 | 1.18 | No | No | NM_001307 | claudin 7 (CLDN7) |
| −2.5 | 6 | 4.31 | −1.59 | No | No | NM_000759 | colony stimulating factor 3 (granulocyte) (CSF3) |
| 17.6 | 1.59 | 7.11 | 30.71 | No | No | NM_003914 | cycHn A1(CCNA1) |
| −3.01 | 6.9 | 1.11 | −1.55 | No | No | NM_000077 | cyclin-dependent kinase inhibitor 2A (melanoma, p16) (CDKN2A) |
| −2.28 | 20.41 | 12.58 | 1.16 | No | Yes | NM_001311 | cysieine-rich protein 1 (intestinal) (CRIP 1) |
| 20.29 | 0.61 | 2.14 | 12.03 | No | Yes | NM_004750 | cytokine receptor-like factor 1 (CRLF1) |
| 5.85 | 0.41 | 2.83 | −1.06 | No | No | AF199015 | cytovillin 2 (VIL2, ezrin) |
| 6.41 | 3.45 | −034 | 0.62 | No | No | AY004154 | DEAD box RNA helicase (VASA) |
| 5.06 | 1.62 | −1.36 | −3.25 | No | No | NM_014326 | death-associated protein kinase 2 (DAPK2) |
| 52.76 | 91.78 | 41.45 | 59.31 | Yes | Yes | NM_001351 | deleted in azoospermia-like (DAZL) |
| 38.06 | 405.04 | 185.65 | 141.23 | Yes | Yes | NM_001472 | G antigen 2 (GAGE2) |
| 26.49 | 275.96 | 149.24 | 129.27 | No | Yes | NM_001477 | G antigen 7B (GAGE7B) |
| 0.49 | 5.02 | −1.98 | 0.4 | No | No | NM_002048 | growth arrest-specific 1 (GAS1) |
| 1.07 | 116.32 | −1.01 | −1.03 | No | Yes | NM_005345 | heat shock 70 kD protein 1A (HSPA1A) |
| 5.49 | −1.1 | 2.39 | 1.55 | No | Yes | NM_030926 | integral membrane protein 3 (ITM3) |
| 1.4 | 5.57 | 10.06 | 1.29 | No | Yes | AF154005 | junction adhesion molecule |
| 7.42 | 4.37 | 3.91 | 0.42 | No | No | NM_KJ0422 | keratin 17 (KRT17) |
| 6.69 | 6.07 | 2.39 | 055 | Yes | No | NM_KW789 | LIM homeobox protein 2 (LHX2) |
| −0.49 | −0.49 | 10.62 | 0.41 | Yes | No | NM_000236 | lipase, hepatic (LIPC) |
| 6.52 | 1.72 | 2.32 | −1.18 | No | No | NM_02424 | matrix metalloproteinase 8 (neutrophil collagenase) (MMP3) |
| 8.46 | 7.88 | 5.95 | 4.31 | No | Yes | NM_005462 | melanoma antigen, family C, 1 (MAGEC1) |
| 1.16 | 5.37 | 1.03 | 1.02 | No | Yes | NM_000249 | mutL (E. coli) homolog 1 (colon cancer, nonpolyposis type 2) (MLH1) |
| 14.18 | 1.67 | 2.89 | 1.09 | Yes | Yes | NM_004221 | natural killer cell transcript 4 (NK4) |
| 5.1 | 10.46 | 16.4 | 14.69 | No | Yes | AF298547 | nucleotide-binding site protein 1 |

TABLE 3-continued

| Fold-change after combined treatment | | | | Induced by 5Aza-dC alone? | Induced by TSA alone? | Genbank# | Gene name (symbol) |
|---|---|---|---|---|---|---|---|
| AsPC1 | Hs766T | MiaPaCa | Panel | | | | |
| 6.8 | 4.51 | 6 | 1.05 | Yes | No | NM_006034 | p53-induced protein (PIG11) |
| 12.42 | 7.96 | −1.27 | 1.22 | Yes | No | NM_000280 | paired box gene 6 (aniridia, keratitis) (PAX6) |
| 10.36 | 18.77 | 1.09 | −1.11 | No | Yes | NM_002727 | proteoglycan 1, secretory granule (PRG1) |
| 9.43 | −1.39 | 11.73 | 4.76 | Yes | No | NM_005978 | S100 calcium-binding protein A2 (S100A2) |
| 3.61 | −0.61 | 7.64 | 18.09 | No | No | NM_005980 | S100 calcium-binding protein P (S100P) |
| 9.24 | 1.83 | 9.38 | 2.08 | Yes | No | NM_002968 | sal (*Drosophila*)-like 1 (SALL1) |
| 3.64 | 7.02 | 1.39 | −1.36 | No | Yes | NM_003919 | sarcoglycan, epsilon (SGCE) |
| 1.57 | −1.69 | 19.85 | −1.39 | Yes | No | AF017987 | secreted apoptosis related protein 2 (SARP2) |
| 5.33 | 1.87 | 1.12 | 1.07 | No | Yes | BC000627 | Signal transducer and activator of transcription 3 (STAT3) |
| 29.63 | 9.56 | 1.23 | 6.25 | No | Yes | NM_022661 | SPANX family, member C (SPANXC) |
| 17.75 | 11.08 | 27.2 | 8.21 | No | Yes | AF257500 | synovial sarcoma, X breakpoint 2 |
| 5.4 | 0.41 | 134 | −1.23 | No | No | NM_003219 | telomerase reverse transcriptase (TERT) |
| 468.96 | 60.57 | 104.53 | 146.17 | No | Yes | X91817 | transketolase-like protein (2418 bp) |
| 17.87 | 11.04 | 6.91 | 6.89 | Yes | Yes | NM_004181 | ubiquitin carboxyl-termninal esterase LI (ubiquitin thiolesterase) (UCHL1) |
| 2.2 | 1.34 | 8.91 | −1.16 | Yes | No | NM_015855 | Wilms tumor associated protein (WIT-1) |
| 6.52 | 1.23 | −1.23 | 4.4 | No | No | NM_003881 | WNTI inducible signaling pathway protein 2 (WISP2) |
| 35.75 | 89.1 | 20.74 | 38.95 | Yes | Yes | NM_020411 | XAGE-1 protein (XAGE-1) |

TABLE 4

| Gene | | | Primer sequences |
|---|---|---|---|
| cadherin 3 (CDH3) | Unmethylated | F | TGT GTG TGG GAG GAT GTA TG |
| | | R | ACA CAT CTA AAATCA ACT AAA AAC |
| | Methylated | F | GCG TGT GGG AGO ACG TAC |
| | | R | ACA TCT AAA ATC GAC TAA AAA CG |
| reprimo | Unmethylated | F | TTG TGA GTG AGT GTT TAG TTT G |
| | | R | TAA TTA CCT AAA ACC AAATTA ATC |
| | Methylated | F | GCG AGT GAG CGT TTA GTT C |
| | | R | TAC CTA AAA CCG AAT TCA TCG |
| claudin 5 (CLDN5) | Unmethylated | F | TGA TAG ATT TGT GGG GTA AAT G |
| | | R | CCC AAA ACC ATA CTA CAC AAC |
| | Methylated | F | GAT AGA TTC GCG GGG TAA AC |
| | | R | TAC GCG ACG CCC TAA ACG |
| death receptor 3 (DR3) | Unmethylated | F | GTT AGG TGG GTT TTT TTT GAT G |
| | | R | TCC ATA ACC CTC CAA CAA AC |
| | Methylated | F | TTA GGC GGG TTT TTT TCG AC |
| | | R | CAT AAC CCT CCG ACG AAC G |
| forkhead box E1 (FOXE1) | Unmethylated | F | TTT GTA GGG TTG GAG ATT TAT G |
| | | R | AAA ACA AAA CAA AAA CAA CAA AAT C |
| | Methylated | F | TCG TAG GGT TGG AGA TTT AC |
| | | R | GAA ACG AAA ACA ACG AAA TCG |
| leucine zipper down-regulated m cancer 1 (LDOC1) | Unmethylated | F | TTA TTA AGT GTT TTT GTG GAT ATG |
| | | R | CCT AAA AAA ACA AAA CTC AAC TC |
| | Methylated | F | TAT TAA GCG TTT TCG TGG ATA C |
| | | R | CGA CCT AAA AAA ACA AAA CTC G |
| LIM homeobox protein 1 (LHX1) | Unmethylated | F | GTG TIT TTT TTG TAA TTT GAG TTT G |
| | | R | AAC CCA CAA AAA AAT AAA AAT CAA C |
| | Methylated | F | GTT TTT TTC GTA ATT CGA GTT C |
| | | R | CGC GAA AAA ATA AAA ATC AAC G |

TABLE 4-continued

| Gene | | | Primer sequences |
|---|---|---|---|
| neurofilament heavy polypeptide (NEFH) | Unmethylated | F | GGT GGT GGT AGT TJT TAT TAT G |
| | | R | ATC CAT ATC CAC AAA TAA AAA CC |
| | Methylated | F | GCG GCG GTA GTT TTT ATT AC |
| | | R | AAA CCG CTA AAA AAA CCA ACG |
| neuronal pentraxinII (NPTX2) | Unmethylated | F | AAG AAA GGG TGT GTG GAT TTG |
| | | R | CCA CAC TAT CAT CTC AAA AAT C |
| | Methylated | F | GAA AGG GCG CGC GGA TTC |
| | | R | CGC TAT CGT CTC GAA AAT CG |
| p53-induced protein (PIGI1) | Unmethylated | F | GTT TGG GTT TGG GAG ATA TTG |
| | | R | CCC CTT TCT TAA AAC AAT CAA C |
| | Methylated | F | GTT TGG GTT CGG GAG ATA TC |
| | | R | CCT TTC TTA AAA CGA TCA ACG r |
| secreted apoptosis related protein 2(SARP2) | Unmethylated | F | GGG TGT ATT TAG TTT GTA GTG |
| | | R | CAA TCC CCC CAA CCA ATA AC |
| | Methylated | F | GTC GGG GCG TAT TTA GTT C |
| | | R | TCC CCC CGA CCA ATA ACG |
| suppression of tumorigenicity 14 (ST14) | Unmethylated | F | GTG TTA GGG TGA GGG TAT TG |
| | | R | ACT CAC AAA TCT CAC AAA CAT C |
| | Methylated | F | CGT TAG GGC GAG GGT ATC |
| | | R | CTC GCG AAT CTC ACA AAC G |
| SWI/SNF-related gene (SMARCA1) | Unmethylated | F | TGT GGA TGT GAT TGT TAT TAT TG |
| | | R | TCT CCA TAA CCA CAA TAA CTT C |
| | Methylated | F | CGG ATG CGA TCG TTA TT A TC |
| | | R | CGT AAC CGC GAT AAC TTC G |
| tight junction protein 2 (TJP2) | Unmethylated | F | TTG TGG GTT AGA GTA TTG TTT G |
| | | R | ATC TCC TCA CAC CAA CAT TTC |
| | Methylated | F | TGC GGG TTA GAG TAT TGT TC |
| | | R | CCT CGC ACCGAC ATT TCG |
| ubiquitin carboxyl-terminal esterase L1 (UCHL1) | Unmethylated | F | TTT GTA TIT ATT TGG TTG TGA TTG |
| | | R | CCC AAA CTA CAA CTA TAA AAC ACC |
| | Methylated | F | TTA TTT GGT CGC GAT CGT TC |
| | | R | CCC AAA CTA CAA CTA TAA AAC G |
| wingless-type MMTV integration site family, member 7A (WNT7A) | Unmethylated | F | TAG TTT GGT GTT GTT TTA TGT TG |
| | | R | CCC CAA AAC CAT CTA TCA ATA C |
| | Methylated | F | GTA GTT CGG CGT CGT TTT AC |
| | | R | CGA AAC CGT CTA TCG ATA CG |

What is claimed is:

1. An amplification primer pair, comprising a forward primer and a reverse primer as set forth in SEQ ID NOS: 5 to 16, 21 to 56, and 61 to 64, wherein the amplification primer pair can amplify a portion of a gene, or associated regulatory region of the gene, selected from the group consisting of reprimo, CLDN5, DR3, LDOC1, LHX1, NEFH, NPTX2, PIG11, SARP2, ST14, SMARCA1, TJP2, and WNT7A, or a combination thereof.

2. The amplification primer pair of claim 1, which can specifically amplify a methylated 5' regulatory region of the nucleic acid molecule.

3. The amplification primer pair of claim 2, comprising SEQ ID NOS: 7 and 8, SEQ ID NOS: 11 and 12, SEQ ID NOS: 15 and 16, SEQ ID NOS: 23 and 24, SEQ ID NOS: 27 and 28, SEQ ID NOS: 31 and 32, SEQ ID NOS: 35 and 36, SEQ ID NOS: 39 and 40, SEQ ID NOS: 43 and 44, SEQ ID NOS: 47 and 48, SEQ ID NOS: 51 and 52, SEQ ID NOS: 55 and 56, or SEQ ID NOS: 63 and 64.

4. An amplification primer pair of claim 1, which can specifically amplify an unmethylated 5' regulatory region of the nucleic acid molecule.

5. The amplification primer pair of claim 4 comprising SEQ ID NOS: 5 and 6, SEQ ID NOS: 9 and 10, SEQ ID NOS: 13 and 14, SEQ ID NOS: 21 and 22, SEQ ID NOS: 25 and 26, SEQ ID NOS: 29 and 30, SEQ ID NOS: 33 and 34, SEQ ID NOS: 37 and 38, SEQ ID NOS: 41 and 42, SEQ ID NOS: 45 and 46, SEQ ID NOS: 49 and 50, SEQ ID NOS: 53 and 54, or SEQ ID NOS: 61 and 62.

6. A kit useful for the detection of pancreatic carcinoma in a subject comprising:
    a) carrier means compartmentalized to receive a sample therein;
    b) one or more containers comprising a first container containing a reagent which modifies unmethylated cytosine and a second container containing primers for amplification of a CpG-containing nucleic acid, wherein the primers are selected from SEQ ID NOS: 5 to 16, 21 to 56, and 61 to 64.

7. The kit of claim 6, further comprising a third container containing a methylation sensitive restriction endonuclease.

8. The kit of claim 6, wherein the modifying reagent is bisulfite.

9. The kit of claim 6, wherein the primers hybridize with a target gene selected from the group consisting of reprimo, CLDN5, DR3, LDOC1, LHX1, NEFH, NPTX2, PIG11, SARP2, ST14, SMARCA1, TJP2, and WNT7A, or a combination thereof.

* * * * *